US010370698B2

(12) United States Patent
Nolan et al.

(10) Patent No.: US 10,370,698 B2
(45) Date of Patent: Aug. 6, 2019

(54) HIGHLY-MULTIPLEXED FLUORESCENT IMAGING

(71) Applicant: The Board of Trustees of the Leland Stanford Junior University, Stanford, CA (US)

(72) Inventors: Garry P. Nolan, Redwood City, CA (US); Nikolay Samusik, Mountain View, CA (US); Julia Kennedy-Darling, Stanford, CA (US); Yury Goltsev, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 39 days.

(21) Appl. No.: 15/660,846

(22) Filed: Jul. 26, 2017

(65) Prior Publication Data
US 2018/0030504 A1 Feb. 1, 2018

Related U.S. Application Data

(60) Provisional application No. 62/367,530, filed on Jul. 27, 2016.

(51) Int. Cl.
*C12Q 1/68* (2018.01)
*C07H 21/00* (2006.01)
*C12Q 1/6804* (2018.01)
*G01N 1/30* (2006.01)
*G01N 33/543* (2006.01)
*G01N 33/554* (2006.01)
*C12Q 1/6813* (2018.01)
*G01N 33/53* (2006.01)

(52) U.S. Cl.
CPC ......... *C12Q 1/6804* (2013.01); *C12Q 1/6813* (2013.01); *G01N 1/30* (2013.01); *G01N 33/5308* (2013.01); *G01N 33/54306* (2013.01); *G01N 33/554* (2013.01); *G01N 2001/302* (2013.01); *G01N 2458/10* (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 5,068,178 A | 11/1991 | Nowinski | |
| 5,985,548 A | 11/1999 | Collier et al. | |
| 6,531,283 B1 | 3/2003 | Kingsmore et al. | |
| 6,743,592 B1 | 6/2004 | Greene et al. | |
| 7,341,831 B2 | 3/2008 | Greene et al. | |
| 7,361,464 B2 | 4/2008 | Greene et al. | |
| 7,846,746 B2 | 12/2010 | Nollau et al. | |
| 8,088,715 B2 | 1/2012 | Bodmer et al. | |
| 8,241,858 B2 | 8/2012 | Eberwine | |
| 8,305,579 B2 | 11/2012 | Treynor et al. | |
| 8,309,306 B2 | 11/2012 | Nolan et al. | |
| 8,445,411 B2 | 5/2013 | Bodmer et al. | |
| 8,530,156 B2 | 9/2013 | Church et al. | |
| 8,658,381 B2 | 2/2014 | Mansson et al. | |
| 8,753,824 B2 | 6/2014 | Papin et al. | |
| 8,946,389 B2 | 2/2015 | Gao et al. | |
| 9,376,717 B2 | 6/2016 | Gao et al. | |
| 9,625,387 B2 | 4/2017 | Demos et al. | |
| 2004/0023271 A1 | 2/2004 | Kurn | |
| 2005/0003360 A1 | 1/2005 | Huang | |
| 2005/0186572 A1 | 8/2005 | Egholm et al. | |
| 2007/0020650 A1 | 1/2007 | Kahvejian | |
| 2007/0026430 A1 | 2/2007 | Andersen et al. | |
| 2007/0148645 A1 | 6/2007 | Hoser | |
| 2008/0317325 A1* | 12/2008 | Ortyn ................. | G01N 15/147 382/133 |
| 2010/0075307 A1 | 3/2010 | Belyaev et al. | |
| 2010/0120043 A1 | 5/2010 | Sood et al. | |
| 2010/0261781 A1 | 10/2010 | Gmeiner | |
| 2011/0033846 A1 | 2/2011 | Dattagupta | |
| 2011/0046359 A1 | 2/2011 | Lee et al. | |
| 2011/0086780 A1 | 4/2011 | Colston, Jr. et al. | |
| 2011/0092381 A1 | 4/2011 | Sood et al. | |
| 2011/0136116 A1 | 6/2011 | Barany et al. | |

(Continued)

FOREIGN PATENT DOCUMENTS

| | | |
|---|---|---|
| EP | 1270738 | 1/2003 |
| EP | 1851331 B1 | 2/2016 |
| WO | WO 01/97616 | 12/2001 |
| WO | WO 2005/054514 | 6/2005 |
| WO | WO2008/052774 | 5/2008 |
| WO | WO 2009/012220 | 1/2009 |
| WO | 2012058638 | 5/2012 |
| WO | WO 2012/057689 | 5/2012 |
| WO | WO2012058638 | 5/2012 |
| WO | WO2012071428 | 5/2012 |

(Continued)

OTHER PUBLICATIONS

Byers et al., J. of Molecular Diagnostics 9 (1) : 20 (Feb. 2007) (Year: 2007).*

(Continued)

*Primary Examiner* — Ethan C Whisenant
(74) *Attorney, Agent, or Firm* — James S. Keddie; Bozicevic, Field & Francis LLP

(57) ABSTRACT

Provided herein is a method and system for analyzing a sample. In some embodiments the method makes use of a plurality of capture agents that are each linked to a different oligonucleotide and a corresponding plurality of labeled nucleic acid probes, wherein each of the labeled nucleic acid probes specifically hybridizes with only one of the oligonucleotides. The sample is labeled with the capture agents en masse, and sub-sets of the capture agents are detected using iterative cycles using corresponding subsets of the labeled nucleic acid probes.

21 Claims, 14 Drawing Sheets
(11 of 14 Drawing Sheet(s) Filed in Color)
Specification includes a Sequence Listing.

(56) References Cited

U.S. PATENT DOCUMENTS

| | | | |
|---|---|---|---|
| 2012/0028242 A1* | 2/2012 | Heyduk | G01N 33/542 |
| | | | 435/5 |
| 2012/0258880 A1* | 10/2012 | Schwartz | C12Q 1/6834 |
| | | | 506/9 |
| 2013/0172213 A1 | 7/2013 | Oliphant et al. | |
| 2013/0323729 A1* | 12/2013 | Landegren | C12Q 1/6804 |
| | | | 435/6.11 |
| 2014/0080126 A1 | 3/2014 | Cantor et al. | |
| 2015/0004598 A1* | 1/2015 | Gao | C12Q 1/6804 |
| | | | 435/6.11 |
| 2015/0005188 A1 | 1/2015 | Levner et al. | |
| 2015/0267251 A1* | 9/2015 | Cai | C12N 15/1065 |
| | | | 506/9 |
| 2015/0309028 A1 | 10/2015 | Jordan | |
| 2015/0368697 A1 | 12/2015 | Samusik et al. | |
| 2016/0161472 A1 | 6/2016 | Jungmann et al. | |
| 2016/0169903 A1 | 6/2016 | Dai et al. | |
| 2016/0319328 A1 | 11/2016 | Yin et al. | |
| 2016/0346330 A1* | 12/2016 | Sussman | A61K 35/34 |
| 2016/0369329 A1* | 12/2016 | Cai | C12Q 1/6841 |
| 2017/0009278 A1 | 1/2017 | Söderberg et al. | |
| 2017/0038391 A1 | 2/2017 | Lara Gutierrez et al. | |
| 2017/0137864 A1 | 5/2017 | Yin et al. | |
| 2017/0151569 A1* | 6/2017 | Handique | B01L 3/502761 |
| 2017/0349949 A1* | 12/2017 | Kolb | C12Q 1/6883 |

FOREIGN PATENT DOCUMENTS

| | | |
|---|---|---|
| WO | WO 2012134602 | 10/2012 |
| WO | WO2013/113699 | 8/2013 |
| WO | WO 2013/188756 | 12/2013 |
| WO | WO 2014/200767 | 12/2014 |
| WO | WO2015017586 | 2/2015 |
| WO | WO 2015/052287 | 4/2015 |
| WO | WO2015188839 | 12/2015 |
| WO | WO 2015200139 | 12/2015 |

OTHER PUBLICATIONS

Chan et al., Current Opinions in Bitechnology 13 : 40 (2002). (Year: 2002).*
Englert et al., Cancer Research 60 :1526 (2000). (Year: 2000).*
Furuya et al., J. of Histochemistry and Cytochemistry 52(2) : 205 (2004). (Year: 2004).*
Gao et al., PNAS 108(9) : 493 (2011 (Year: 2011).*
Han et al., Bioconjugate Chem. 21 :2190(2010). (Year: 2010).*
Huang et al., Nano Res 3:61 (2010). (Year: 2010).*
Larson et al., Pathology Research Intl. 2010 Article ID : 814176. (Year: 2010).*
Saiki et al., Nature 324: 163 (1986). (Year: 1986).*
True et al., J. of Molecular Diagnostics 9 (1) : 7 (Feb. 2007). (Year: 2007).*
Wahlby et al., Cytometry 47 :32 (2002). (Year: 2002).*
Zrazhevskiy and Gao, Nature Communications p. 1-12 ( Mar. 2013) (Year: 2013).*
Arakawa et al. Protein precipitation and denaturation by dimethyl sulfoxid. Biophysical Chemistry 131:62. (Year: 2007).*
Asakura et al.,Stabilizing effect of various Organic Solvents on Protein. J. of Biological Chemistry 253(18) : 6423. (Year: 1978).*
Dhillon et al., "Homogeneous and digital proximity ligation assays for the detection of Clostridium difficile toxins A and B", Biomolecular Detection and Quantification, 2016, 10:2-8.
Shahi et al., "Abseq: Ultrahigh-throughput single cell protein profiling with droplet microfluidic barcoding", Scientific Reports, 2017, 7:44447, DOI: 10.1038/srep44447.
Zhang et al., "Protein quantification from complex protein mixtures using a proteomics methodology with single-cell resolution", PNAS, 2001, 98(10): 5497-5502.
Zhang et al., "A sensitive and high-throughput assay to detect low-abundance proteins in serum", Nature Medicine, 2006, 12(4): 473-477.
Boom D. et al., "Multiplex protein detection with DNA readout via mass spectrometry" N Biotechnol. (2013) 30(2):153-158.
Kazone S.A. et al., "Site-specfic DNA-antibody conjugates for specific and sensitive immuno-PCR" Prod Natl Arad Sci (2012) 109(10):3731-6.
Flor et al., "DNA-Directed Assembly of Antibody-Fluorophore Conjugates for Quantitative Multiparametric Flow Cytometry", Chembiochem, 2013, 15(2): 267-275.
Lundberg et al., "Homogeneous antibody-based proximity extension assays provide sensitive and specific detection of low-abundant proteins in human blood", Nucleic Acids Research, 2011, 39(15): e102.
Niemeyer et al., "Detecting antigens by quantitative immuno-PCR", Nature Protocols, 2007, 2(8): 1918-1930.
Tran et al., "A Universal DNA-Based Protein Detection System", Journal of the American Chemical Society, 2013, 135(38): 14008-14011.
Ullal et al., "Cancer Cell Profiling by Barcoding Allows Multiplexed Protein Analysis in Fine-Needle Aspirates", Science Translational Medicine, 2014, 6(219): 219ra9.
Lubeck et al., "Signle cell systems biology by super-resolution imaging and combinatorial labeling", Nat Methods., Jan. 1, 2013; 9(7): 743-748.

\* cited by examiner

| | | Within a cycle across top oligonucleotides | | | | | | | | | | | | | |
|---|---|---|---|---|---|---|---|---|---|---|---|---|---|---|---|
| | | T1 | T2 | T3 | T4 | T5 | T6 | T7 | T8 | T9 | T10 | T11 | T12 | T13 | T14 | T15 |
| | T1 | 20455 | 2192 | 2815 | 1985 | 2126 | 2515 | 2368 | 2408 | 2131 | 2059 | 2224 | 2205 | 2252 | 2316 | 2365 |
| | T2 | 2192 | 50721 | 2169 | 1921 | 1890 | 2174 | 1993 | 2045 | 2028 | 1989 | 1958 | 1948 | 2049 | 1959 | 2003 |
| | T3 | 5006 | 4715 | 49524 | 4987 | 4866 | 5353 | 5734 | 4906 | 4842 | 4696 | 4766 | 5875 | 5317 | 4824 | 5152 |
| | T4 | 11929 | 10786 | 11226 | 36648 | 11920 | 12393 | 12116 | 11520 | 11670 | 11226 | 10711 | 11320 | 11812 | 12385 | 12845 |
| | T5 | 1745 | 1500 | 1585 | 1588 | 55369 | 1884 | 1678 | 1757 | 1640 | 1575 | 1483 | 1761 | 1689 | 1784 | 1759 |
| | T6 | 12073 | 11307 | 11600 | 11780 | 11321 | 25700 | 12445 | 12940 | 11699 | 11086 | 10826 | 11491 | 12412 | 11959 | 12673 |
| | T7 | 4639 | 4811 | 4690 | 4602 | 4518 | 4812 | 45607 | 5011 | 4779 | 4681 | 4444 | 5564 | 4742 | 4389 | 4888 |
| | T8 | 1309 | 1279 | 1180 | 1269 | 1328 | 1453 | 1388 | 40766 | 1378 | 1370 | 1279 | 1294 | 1362 | 1263 | 1498 |
| Single cell across cycles | T9 | 9275 | 5326 | 5566 | 6363 | 7181 | 8530 | 7761 | 5794 | 42186 | 40221 | 4927 | 6355 | 6800 | 5636 | 7285 |
| | T10 | 8878 | 8041 | 7678 | 9029 | 9292 | 9646 | 9693 | 8899 | 40429 | 40531 | 8334 | 8748 | 9219 | 8523 | 9124 |
| | T11 | 938.6 | 983.2 | 975 | 985.4 | 916.8 | 1072 | 951.9 | 1071 | 954.2 | 917.8 | 38705 | 1055 | 1201 | 1529 | 1194 |
| | T12 | 9338 | 7993 | 10428 | 8701 | 9413 | 10390 | 10487 | 8822 | 9402 | 8928 | 8043 | 48087 | 10533 | 8773 | 9962 |
| | T13 | 6160 | 5694 | 5803 | 5788 | 5499 | 6003 | 5977 | 5603 | 5783 | 5756 | 5589 | 5684 | 21617 | 6164 | 5987 |
| | T14 | 1259 | 1192 | 1220 | 1137 | 1272 | 1281 | 1276 | 1222 | 1202 | 1207 | 1173 | 1177 | 1293 | 36438 | 1404 |
| | T15 | 4905 | 4904 | 5006 | 4848 | 4840 | 5321 | 5240 | 5174 | 4997 | 4943 | 6397 | 4989 | 5350 | 4639 | 44248 |
| | T16 | 4448 | 4748 | 4534 | 4507 | 4778 | 4811 | 4649 | 4687 | 4646 | 4686 | 4591 | 4855 | 4673 | 4295 | 4735 |
| | T17 | 4131 | 3696 | 4515 | 3817 | 3958 | 4394 | 4193 | 4001 | 3990 | 4000 | 3618 | 3956 | 4105 | 3776 | 4105 |
| | T18 | 2016 | 13577 | 2042 | 2079 | 2485 | 2237 | 2252 | 2858 | 2193 | 2181 | 2109 | 2498 | 2321 | 2226 | 2172 |
| | T19 | 11206 | 10479 | 10232 | 10772 | 11325 | 12466 | 11823 | 10505 | 10914 | 11106 | 11142 | 11571 | 12352 | 11178 | 10981 |
| | T20 | 2812 | 2543 | 2412 | 2722 | 2716 | 2927 | 3413 | 2922 | 3054 | 3284 | 2847 | 2795 | 3008 | 3367 | 2791 |
| | T21 | 5262 | 5404 | 5468 | 5104 | 5095 | 5576 | 5222 | 5668 | 5421 | 5232 | 5265 | 5520 | 5859 | 5304 | 5231 |
| | T22 | 8328 | 7888 | 8300 | 7994 | 8148 | 9069 | 8798 | 8421 | 8620 | 8541 | 8251 | 8322 | 8775 | 8233 | 8361 |
| | T23 | 6254 | 5975 | 6105 | 5915 | 5959 | 6499 | 6093 | 6164 | 6057 | 6515 | 6423 | 6249 | 6531 | 6287 | 6184 |
| | T24 | 4691 | 4611 | 4253 | 4457 | 4615 | 4753 | 4932 | 4498 | 4537 | 4671 | 4344 | 4450 | 4813 | 4328 | 4700 |
| | T25 | 3209 | 3254 | 3381 | 3169 | 3318 | 3136 | 3234 | 3255 | 2914 | 2968 | 3471 | 3754 | 3540 | 3240 | 3123 |
| | T26 | 2195 | 2541 | 2283 | 2101 | 2426 | 2154 | 2636 | 2264 | 2164 | 2224 | 2238 | 2285 | 2397 | 2003 | 2167 |
| | T27 | 1426 | 1320 | 1238 | 1490 | 1598 | 1459 | 1616 | 1582 | 1892 | 2047 | 1572 | 1482 | 1657 | 1665 | 1415 |
| | T28 | 3558 | 3486 | 3685 | 3299 | 3663 | 3705 | 3428 | 3709 | 3396 | 3238 | 3595 | 3329 | 3638 | 3369 | 3522 |
| | T29 | 10921 | 10949 | 10501 | 10629 | 10431 | 10947 | 11538 | 10534 | 10391 | 10691 | 9972 | 10260 | 10887 | 10874 | 11058 |
| | T30 | 1210 | 1186 | 1141 | 1037 | 1420 | 1213 | 1239 | 1252 | 1116 | 1179 | 1145 | 1318 | 1208 | 1154 | 1187 |

FIG. 8

| T16 | T17 | T18 | T19 | T20 | T21 | T22 | T23 | T24 | T25 | T26 | T27 | T28 | T29 | T30 |
|---|---|---|---|---|---|---|---|---|---|---|---|---|---|---|
| 2342 | 2464 | 2176 | 1978 | 2185 | 2538 | 2423 | 2074 | 2375 | 2345 | 2234 | 2290 | 2198 | 2359 | 2365 |
| 2118 | 1981 | 2027 | 1788 | 2087 | 2104 | 2010 | 1878 | 1955 | 2111 | 2081 | 1826 | 1900 | 1980 | 1982 |
| 5433 | 4973 | 4460 | 4386 | 4955 | 5055 | 5068 | 4534 | 5169 | 4931 | 5279 | 4515 | 4465 | 5262 | 4607 |
| 12112 | 12914 | 10822 | 10939 | 11631 | 11981 | 12661 | 11652 | 11339 | 11458 | 11962 | 12053 | 11855 | 11413 | 11692 |
| 1732 | 1779 | 1621 | 1556 | 1647 | 1766 | 1856 | 1667 | 1740 | 1601 | 1640 | 1856 | 1695 | 1684 | 2184 |
| 11900 | 12659 | 11240 | 10739 | 11420 | 12042 | 12152 | 11158 | 11498 | 11161 | 11565 | 11225 | 10840 | 11517 | 11368 |
| 4675 | 4779 | 4620 | 4076 | 4743 | 4959 | 4642 | 4198 | 4621 | 4559 | 4785 | 4276 | 4358 | 4614 | 4270 |
| 1366 | 1342 | 1252 | 1103 | 1249 | 1273 | 1344 | 1117 | 1276 | 1349 | 1247 | 1197 | 1203 | 1276 | 1218 |
| 8447 | 5755 | 5777 | 4593 | 5902 | 5241 | 7659 | 5940 | 4353 | 5001 | 9480 | 6666 | 5464 | 4290 | 3572 |
| 9879 | 8619 | 8750 | 7677 | 8569 | 8587 | 10548 | 8815 | 7472 | 8389 | 10552 | 8995 | 8763 | 7486 | 7091 |
| 1045 | 986.1 | 990.1 | 884.3 | 1028 | 1015 | 1066 | 935 | 1010 | 981.6 | 997.4 | 900.6 | 974.7 | 998 | 959.4 |
| 10619 | 9869 | 8683 | 7895 | 8868 | 8937 | 10439 | 9083 | 8121 | 8624 | 10183 | 9202 | 8715 | 8178 | 7593 |
| 6663 | 5953 | 6058 | 5457 | 5970 | 6072 | 6066 | 5607 | 5921 | 6112 | 5855 | 5560 | 5840 | 5895 | 5719 |
| 1244 | 1260 | 1173 | 1070 | 1190 | 1454 | 1327 | 1029 | 1155 | 1292 | 1323 | 1177 | 1164 | 1148 | 1245 |
| 6070 | 4733 | 5175 | 4572 | 4936 | 5186 | 5054 | 4791 | 4806 | 4856 | 5045 | 8432 | 4740 | 4634 | 4878 |
| 43923 | 4658 | 4666 | 5048 | 4639 | 4346 | 4572 | 4141 | 4604 | 4581 | 4730 | 4313 | 4320 | 4629 | 4404 |
| 3902 | 32848 | 4293 | 3594 | 3860 | 3995 | 4049 | 3852 | 3738 | 3894 | 4124 | 3716 | 3957 | 3727 | 4591 |
| 2676 | 2274 | 34476 | 1944 | 2003 | 2152 | 2803 | 15305 | 2274 | 2388 | 2569 | 2299 | 2099 | 2200 | 2484 |
| 12321 | 11889 | 10839 | 27681 | 14745 | 10814 | 13760 | 11585 | 11016 | 12284 | 12763 | 11682 | 10999 | 10906 | 10917 |
| 3201 | 2878 | 6913 | 2596 | 31054 | 3022 | 3578 | 3171 | 2704 | 3056 | 3872 | 3110 | 3179 | 2705 | 2670 |
| 5679 | 5596 | 5349 | 4751 | 5461 | 46930 | 6893 | 4978 | 5411 | 5636 | 5446 | 4907 | 4867 | 5468 | 5146 |
| 8563 | 8526 | 8311 | 7648 | 8483 | 8685 | 15729 | 8384 | 8896 | 8980 | 8790 | 8405 | 8175 | 8822 | 8556 |
| 6442 | 6096 | 6011 | 5823 | 6338 | 6674 | 6848 | 38444 | 6668 | 6956 | 6588 | 5958 | 6425 | 6665 | 6698 |
| 4444 | 5156 | 4321 | 4137 | 4843 | 4661 | 5011 | 4250 | 48651 | 4798 | 4952 | 4294 | 4611 | 48488 | 4154 |
| 3653 | 2960 | 3375 | 3611 | 3796 | 3185 | 3685 | 3518 | 3140 | 56082 | 3952 | 3499 | 3652 | 3124 | 3159 |
| 2079 | 2661 | 2218 | 2102 | 2427 | 2207 | 2320 | 2020 | 5128 | 2207 | 47232 | 2525 | 2113 | 5117 | 2084 |
| 1708 | 1404 | 4200 | 1332 | 1897 | 1398 | 1737 | 1546 | 1340 | 1889 | 1841 | 38929 | 1759 | 1336 | 1258 |
| 3652 | 3567 | 3584 | 3394 | 3587 | 4092 | 3689 | 3869 | 3431 | 10064 | 3938 | 3879 | 36456 | 3462 | 3628 |
| 10667 | 11846 | 10793 | 10149 | 11099 | 10802 | 12161 | 10948 | 29731 | 11157 | 28995 | 11224 | 11624 | 29745 | 11996 |
| 1382 | 1456 | 2038 | 1082 | 1442 | 1239 | 1336 | 1220 | 1115 | 1458 | 1334 | 6650 | 1341 | 1153 | 28682 |

FIG. 8 (Cont.)

SEQUENCE LISTING

<160> NUMBER OF SEQ ID NOS: 94

<210> SEQ ID NO 1
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 1
ttagacaact ttagt                                                      15

<210> SEQ ID NO 2
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 2
catcaggatt tggta                                                      15

<210> SEQ ID NO 3
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 3
cgctcctcat gataa                                                      15

<210> SEQ ID NO 4
<211> LENGTH: 13
<212> TYPE: DNA
<213> ORGANISM: Artificial sequence
<220> FEATURE:
<223> OTHER INFORMATION: synthetic nucleic acid

<400> SEQUENCE: 4
cggccatcca tta                                                        13

<210> SEQ ID NO 5
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 5
ggctgattac cctct                                                      15

<210> SEQ ID NO 6
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 6
tagcattgtg taggt                                                      15

<210> SEQ ID NO 7
<211> LENGTH: 17
<212> TYPE: DNA
<213> ORGANISM: Artificial sequence
<220> FEATURE:
<223> OTHER INFORMATION: synthetic nucleic acid

<400> SEQUENCE: 7
gaatcttata gaatcgc                                                      17

<210> SEQ ID NO 8
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 8
cttataagta gacgc                                                        15

<210> SEQ ID NO 9
<211> LENGTH: 14
<212> TYPE: DNA
<213> ORGANISM: Artificial sequence
<220> FEATURE:
<223> OTHER INFORMATION: synthetic nucleic acid

<400> SEQUENCE: 9
ctgggcgaga tatg                                                         14

<210> SEQ ID NO 10
<211> LENGTH: 11
<212> TYPE: DNA
<213> ORGANISM: Artificial sequence
<220> FEATURE:
<223> OTHER INFORMATION: synthetic nucleic acid

<400> SEQUENCE: 10
ctcggcccga t                                                            11

<210> SEQ ID NO 11
<211> LENGTH: 17
<212> TYPE: DNA
<213> ORGANISM: Artificial sequence
<220> FEATURE:
<223> OTHER INFORMATION: synthetic nucleic acid

<400> SEQUENCE: 11
agattactac tcataca                                                      17

<210> SEQ ID NO 12
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 12
gctctctgac ttaga                                                        15

<210> SEQ ID NO 13
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 13
atcacggata atgtc                                                        15

```
<210> SEQ ID NO 14
<211> LENGTH: 17
<212> TYPE: DNA
<213> ORGANISM: Artificial sequence
<220> FEATURE:
<223> OTHER INFORMATION: synthetic nucleic acid

<400> SEQUENCE: 14
agtactaata gtagtga                                                  17

<210> SEQ ID NO 15
<211> LENGTH: 12
<212> TYPE: DNA
<213> ORGANISM: Artificial sequence
<220> FEATURE:
<223> OTHER INFORMATION: synthetic nucleic acid

<400> SEQUENCE: 15
tggcattctg gc                                                       12

<210> SEQ ID NO 16
<211> LENGTH: 14
<212> TYPE: DNA
<213> ORGANISM: Artificial sequence
<220> FEATURE:
<223> OTHER INFORMATION: synthetic nucleic acid

<400> SEQUENCE: 16
ctcaggttcg agtc                                                     14

<210> SEQ ID NO 17
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 17
ctctggtagg atgta                                                    15

<210> SEQ ID NO 18
<211> LENGTH: 13
<212> TYPE: DNA
<213> ORGANISM: Artificial sequence
<220> FEATURE:
<223> OTHER INFORMATION: synthetic nucleic acid

<400> SEQUENCE: 18
cactttgccg tgc                                                      13

<210> SEQ ID NO 19
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 19
gatacgaggc gttat                                                    15

<210> SEQ ID NO 20
<211> LENGTH: 15
<212> TYPE: DNA
<213> ORGANISM: Artificial sequence
<220> FEATURE:
<223> OTHER INFORMATION: synthetic nucleic acid
```

```
<400> SEQUENCE: 20
cacagactcc tttgg                                                  15

<210> SEQ ID NO 21
<211> LENGTH: 13
<212> TYPE: DNA
<213> ORGANISM: Artificial sequence
<220> FEATURE:
<223> OTHER INFORMATION: synthetic nucleic acid

<400> SEQUENCE: 21
attttcccgc acg                                                    13

<210> SEQ ID NO 22
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 22
atgcaatcac ctggt                                                  15

<210> SEQ ID NO 23
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 23
gaagtttacg ggata                                                  15

<210> SEQ ID NO 24
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 24
actaagcgag tacac                                                  15

<210> SEQ ID NO 25
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 25
aatctgttga aatca                                                  15

<210> SEQ ID NO 26
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 26
gtagtcctaa accat                                                  15

<210> SEQ ID NO 27
```

```
<211> LENGTH: 12
<212> TYPE: DNA
<213> ORGANISM: Artificial sequence
<220> FEATURE:
<223> OTHER INFORMATION: synthetic nucleic acid

<400> SEQUENCE: 27
cggcgaggag ta                                                              12

<210> SEQ ID NO 28
<211> LENGTH: 12
<212> TYPE: DNA
<213> ORGANISM: Artificial sequence
<220> FEATURE:
<223> OTHER INFORMATION: synthetic nucleic acid

<400> SEQUENCE: 28
acgccggtag gt                                                              12

<210> SEQ ID NO 29
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 29
ccgactaatg ggaga                                                           15

<210> SEQ ID NO 30
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 30
atcgtaacac atcca                                                           15

<210> SEQ ID NO 31
<211> LENGTH: 17
<212> TYPE: DNA
<213> ORGANISM: Artificial sequence
<220> FEATURE:
<223> OTHER INFORMATION: synthetic nucleic acid

<400> SEQUENCE: 31
cttagaatat cttagcg                                                         17

<210> SEQ ID NO 32
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 32
gaatattcat ctgcg                                                           15

<210> SEQ ID NO 33
<211> LENGTH: 14
<212> TYPE: DNA
<213> ORGANISM: Artificial sequence
<220> FEATURE:
<223> OTHER INFORMATION: synthetic nucleic acid

<400> SEQUENCE: 33
```
ctatcgtccg tgca                                                14

<210> SEQ ID NO 34
<211> LENGTH: 12
<212> TYPE: DNA
<213> ORGANISM: Artificial sequence
<220> FEATURE:
<223> OTHER INFORMATION: synthetic nucleic acid

<400> SEQUENCE: 34
gagccgggct ag                                                  12

<210> SEQ ID NO 35
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 35
cgagagactg aatct                                               15

<210> SEQ ID NO 36
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 36
tagtgcctat tacag                                               15

<210> SEQ ID NO 37
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 37
tcatgattat catca                                               15

<210> SEQ ID NO 38
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 38
accgtaagac cgctt                                               15

<210> SEQ ID NO 39
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 39
gagtccaagc tcagc                                               15

<210> SEQ ID NO 40
<211> LENGTH: 15
<212> TYPE: DNA

<213> ORGANISM: Artificial sequence
<220> FEATURE:
<223> OTHER INFORMATION: synthetic nucleic acid

<400> SEQUENCE: 40
gagaccatcc tacat							15

<210> SEQ ID NO 41
<211> LENGTH: 13
<212> TYPE: DNA
<213> ORGANISM: Artificial sequence
<220> FEATURE:
<223> OTHER INFORMATION: synthetic nucleic acid

<400> SEQUENCE: 41
gtgaaacggc acg							13

<210> SEQ ID NO 42
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 42
ctatgctccg caata							15

<210> SEQ ID NO 43
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 43
gtgtctgagg aaacc							15

<210> SEQ ID NO 44
<211> LENGTH: 13
<212> TYPE: DNA
<213> ORGANISM: Artificial sequence
<220> FEATURE:
<223> OTHER INFORMATION: synthetic nucleic acid

<400> SEQUENCE: 44
taaaagggcg tgc							13

<210> SEQ ID NO 45
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 45
tacgttagtg gacca							15

<210> SEQ ID NO 46
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 46
cttcaaatgc cctat							15

<210> SEQ ID NO 47
<211> LENGTH: 15
<212> TYPE: DNA
<213> ORGANISM: Artificial sequence
<220> FEATURE:
<223> OTHER INFORMATION: synthetic nucleic acid

<400> SEQUENCE: 47
tgattcgctc atgtg                                                        15

<210> SEQ ID NO 48
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 48
atagcagtcc agcgcccac taaagttgtc taa                                     33

<210> SEQ ID NO 49
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 49
atagcagtcc agaacgacta ccaaatcctg atg                                    33

<210> SEQ ID NO 50
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 50
atagcagtcc agctattatc atgaggagcg gcg                                    33

<210> SEQ ID NO 51
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 51
atagcagtcc aggatcttaa tggatggccg cag                                    33

<210> SEQ ID NO 52
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 52
atagcagtcc agcgggtgag agggtaatca gcc                                    33

<210> SEQ ID NO 53
<211> LENGTH: 33
<212> TYPE: DNA
<213> ORGANISM: Artificial sequence
<220> FEATURE:

<223> OTHER INFORMATION: synthetic nucleic acid

<400> SEQUENCE: 53
atagcagtcc aggtgtccac ctacacaatg cta            33

<210> SEQ ID NO 54
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 54
atagcagtcc agtcgggcga ttctataaga ttc            33

<210> SEQ ID NO 55
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 55
atagcagtcc agcgcattgc gtctacttat aag            33

<210> SEQ ID NO 56
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 56
atagcagtcc agttaaacgc atatctcgcc cag            33

<210> SEQ ID NO 57
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 57
atagcagtcc agtcattcgt agatcgggcc gag            33

<210> SEQ ID NO 58
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 58
atagcagtcc agttactgta tgagtagtaa tct            33

<210> SEQ ID NO 59
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 59
atagcagtcc aggctacctc taagtcagag agc            33

<210> SEQ ID NO 60
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 60
atagcagtcc aggctcgtga cattatccgt gat                                    33

<210> SEQ ID NO 61
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 61
atagcagtcc agtttctcac tactattagt act                                    33

<210> SEQ ID NO 62
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 62
atagcagtcc agccttgttt cgccagaatg cca                                    33

<210> SEQ ID NO 63
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 63
atagcagtcc agctcttccg actcgaacct gag                                    33

<210> SEQ ID NO 64
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 64
atagcagtcc agttagccta catcctacca gag                                    33

<210> SEQ ID NO 65
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 65
atagcagtcc agcatggcct gcacggcaaa gtg                                    33

<210> SEQ ID NO 66
<211> LENGTH: 33
<212> TYPE: DNA
<213> ORGANISM: Artificial sequence
<220> FEATURE:
<223> OTHER INFORMATION: synthetic nucleic acid

```
<400> SEQUENCE: 66
atagcagtcc agatggcaat aacgcctcgt atc                         33

<210> SEQ ID NO 67
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 67
atagcagtcc aggaagcgcc aaaggagtct gtg                         33

<210> SEQ ID NO 68
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 68
atagcagtcc agtccgtctc cgtgcgggaa aat                         33

<210> SEQ ID NO 69
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 69
atagcagtcc agatactaac caggtgattg cat                         33

<210> SEQ ID NO 70
<211> LENGTH: 33
<212> TYPE: DNA
<213> ORGANISM: Artificial sequence
<220> FEATURE:
<223> OTHER INFORMATION: synthetic nucleic acid

<400> SEQUENCE: 70
atagcagtcc aggcgcacta tcccgtaaac ttc                         33

<210> SEQ ID NO 71
<211> LENGTH: 34
<212> TYPE: DNA
<213> ORGANISM: Artificial sequence
<220> FEATURE:
<223> OTHER INFORMATION: synthetic nucleic acid

<400> SEQUENCE: 71
atagcagtcc aggggcatgt gtactcgctt agtr                        34

<210> SEQ ID NO 72
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 72
atagcagtcc aggcggggtg atttcaacag attaa                       35

<210> SEQ ID NO 73
<211> LENGTH: 35
```

<212> TYPE: DNA
<213> ORGANISM: Artificial sequence
<220> FEATURE:
<223> OTHER INFORMATION: synthetic nucleic acid

<400> SEQUENCE: 73
atagcagtcc agttgctgat ggtttaggac tacgg        35

<210> SEQ ID NO 74
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 74
atagcagtcc aggataatag tactcctcgc cgcaa        35

<210> SEQ ID NO 75
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 75
atagcagtcc agctagaatt acctaccggc gtcgg        35

<210> SEQ ID NO 76
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 76
atagcagtcc aggcccactc tcccattagt cggaa        35

<210> SEQ ID NO 77
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 77
atagcagtcc agcacaggtg gatgtgttac gatgg        35

<210> SEQ ID NO 78
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 78
atagcagtcc agagcccgct aagatattct aagtt        35

<210> SEQ ID NO 79
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 79
atagcagtcc aggcgtaacg cagatgaata ttcaa                         35

<210> SEQ ID NO 80
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 80
atagcagtcc agaatttgcg tatagagcgg gtcaa                         35

<210> SEQ ID NO 81
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 81
atagcagtcc agagtaagca tctagcccgg ctctt                         35

<210> SEQ ID NO 82
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 82
atagcagtcc agcgatggag attcagtctc tcggg                         35

<210> SEQ ID NO 83
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 83
atagcagtcc agcgagcact gtaataggca ctatt                         35

<210> SEQ ID NO 84
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 84
atagcagtcc agaaagagtg atgataatca tgaaa                         35

<210> SEQ ID NO 85
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 85
atagcagtcc agggaacaaa gcggtcttac ggttt                         35

<210> SEQ ID NO 86
<211> LENGTH: 35
<212> TYPE: DNA
<213> ORGANISM: Artificial sequence

```
<220> FEATURE:
<223> OTHER INFORMATION: synthetic nucleic acid

<400> SEQUENCE: 86
atagcagtcc aggagaaggc tgagcttgga ctcaa                              35

<210> SEQ ID NO 87
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 87
atagcagtcc agaatcggat gtaggatggt ctcgg                              35

<210> SEQ ID NO 88
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 88
atagcagtcc aggtaccgga cgtgccgttt cactt                              35

<210> SEQ ID NO 89
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 89
atagcagtcc agtaccgtta ttgcggagca taggg                              35

<210> SEQ ID NO 90
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 90
atagcagtcc agcttcgcgg tttcctcaga cacgg                              35

<210> SEQ ID NO 91
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 91
atagcagtcc agaggcagag gcacgccctt ttaaa                              35

<210> SEQ ID NO 92
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 92
atagcagtcc agtatgattg gtccactaac gtagg                              35
```

```
<210> SEQ ID NO 93
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 93
atagcagtcc agcgcgtgat agggcatttg aaggg                              35

<210> SEQ ID NO 94
<211> LENGTH: 35
<212> TYPE: DNA
<213> ORGANISM: Artificial sequence
<220> FEATURE:
<223> OTHER INFORMATION: synthetic nucleic acid

<400> SEQUENCE: 94
atagcagtcc agcccgtaca catgagcgaa tcagg                              35
```

HIGHLY-MULTIPLEXED FLUORESCENT IMAGING

CROSS-REFERENCING

This application claims the benefit of U.S. provisional application Ser. No. 62/367,530, filed on Jul. 27, 2016, which application is incorporated by reference herein.

GOVERNMENT SUPPORT

This invention was made with Government support under contract HHSF223201210194C awarded by the The Food and Drug Administration. The Government has certain rights in the invention.

BACKGROUND

Antibodies were first employed in tissue section analysis in 1942 to visualize pneumococcal antigens in organ biopsies from mice infused with live bacteria. Since that time, immunohistochemistry has become a mainstay of clinical diagnostics and basic research.

However, conventional immunohistochemistry methods are limited in that they are only able to assess the spatial distribution of one, two or three (rarely more) epitopes in a tissue section. This constraint limits the application of immunohistochemistry in clinical diagnostics, in which field it is very desirable to analyze a much larger number of epitopes. Newer methods for epitope detection in a sample have been described and involve, for example, labeling a capture agent with DNA and subsequently detecting this DNA by primer extension, e.g., as in WO 2015/200139 and US 20150368697.

The present method is automatable and allows for a highly multiplexed analysis. As such, the method is believed to meet some of the deficiencies of conventional immunohistochemistry methods.

SUMMARY

Provided herein is a method for analyzing a sample. In some embodiments, the method makes use of a plurality of capture agents that are each linked to a different oligonucleotide and a corresponding plurality of labeled nucleic acid probes, wherein each of the labeled nucleic acid probes specifically hybridizes with only one of the oligonucleotides. The sample is labeled with the capture agents en masse, and sub-sets of the capture agents are detected using iterative hybridization/label removal or inactivation cycles using corresponding subsets of the labeled nucleic acid probes. In some embodiments the capture agents are not stripped from the sample between hybridization/de-hybridization cycles. Depending on how the method is implemented, the method can be used to detect more than 40 epitopes in a sample without needing to strip the capture agents from the sample.

BRIEF DESCRIPTION OF THE FIGURES

The patent or application file contains at least one drawing executed in color. Copies of this patent or patent application publication with color drawing(s) will be provided by the Office upon request and payment of the necessary fee.

The skilled artisan will understand that the drawings, described below, are for illustration purposes only. The drawings are not intended to limit the scope of the present teachings in any way.

FIG. 8: Cross-hybridization matrix. Cross-hybridization between the library of dye-labeled oligonucleotides and oligonucleotides conjugated to CD45 antibodies was screened. Oligonucleotide pairs with cross-hybridization have fluorescence intensity off-diagonal.

DEFINITIONS

Figure 1:
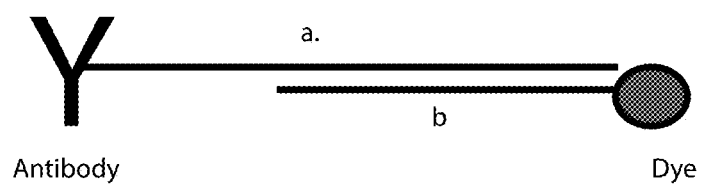
FIG. 1: Each antibody is conjugated to an oligonucleotide 38-40 nt in length (a), which complements a shorter dye-labeled oligonucleotide (b).

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "biological feature of interest" refers to any part of a cell that can be indicated by binding to a capture agent. Exemplary biological features of interest include cell walls, nuclei, cytoplasm, membrane, keratin, muscle fibers, collagen, bone, proteins, nucleic acid (e.g., mRNA or genomic DNA, etc), fat, etc. A biological feature of interest can also be indicated by immunohistological methods, e.g., a capture agent that is linked to an oligonucleotide. In these embodiments, the capture agent binds to a site, e.g., a protein epitope, in the sample. Exemplary epitopes include, but are not limited to, carcinoembryonic antigen (for identification of adenocarcinomas), cytokeratins (for identification of carcinomas but may also be expressed in some sarcomas) CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumour identification), CD20 (for identification of B-cell lymphomas), CD3 (for identification of T-cell lymphomas).

As used herein, the term "multiplexing" refers to using more than one label for the simultaneous or sequential detection and measurement of biologically active material.

As used herein, the terms "antibody" and "immunoglobulin" are used interchangeably herein and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (IgG$_1$, IgG$_2$, IgG$_3$, IgG$_4$), delta, epsilon and mu heavy chains or equivalents in other species. Full-length immunoglobulin "light chains" (of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, minibodies, single-chain antibodies, and fusion proteins comprising an antigen-binding portion of an antibody and a non-antibody protein. Also encompassed by the term are Fab', Fv, F(ab')$_2$, and or other antibody fragments that retain specific binding to antigen, and monoclonal antibodies. Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e. g., Huston et al., Proc. Natl. Acad. Sci. U.S.A., 85, 5879-5883 (1988) and Bird et al., Science, 242, 423-426 (1988)), which are incorporated herein by reference. (See, generally, Hood et al., "Immunology", Benjamin, N.Y., 2nd ed. (1984), and Hunkapiller and Hood, Nature, 323, 15-16 (1986)).

The term "specific binding" refers to the ability of a binding reagent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a binding reagent and analyte when they are specifically bound in a capture agent/analyte complex is characterized by a K$_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

A "plurality" contains at least 2 members. In certain cases, a plurality may have at least 2, at least 5, at least 10, at least 100, at least 1000, at least 10,000, at least 100,000, at least $10^6$, at least $10^7$, at least $10^8$ or at least $10^9$ or more members.

As used herein, the term "labeling" refers to attaching a capture agent to specific sites in a sample (e.g., sites containing an epitope for the antibody being used, for example) such that the presence and/or abundance of the sites can be determined by evaluating the presence and/or abundance of the capture agent. The term "labeling" refers to a method for producing a labeled sample in which any necessary steps are performed in any convenient order, as long as the required labeled sample is produced. For example, in some embodiments and as will be exemplified below, the capture agent may be linked to an oligonucleotide prior to binding of the antibody to the sample, in which case a sample can be labeled using relatively few steps.

As used herein, the term "planar sample" refers to a substantially planar, i.e., two dimensional, material (e.g. glass, metal, ceramics, organic polymer surface or gel) that contains cells or any combination of biomolecules derived from cells, such as proteins, nucleic acids, lipids, oligo/polysachharides, biomolecule complexes, cellular organelles, cellular debris or excretions (exosomes, microvesicles). A planar cellular sample can be made by, e.g., growing cells on a planar surface, depositing cells on a planar surface, e.g., by centrifugation, by cutting a three dimensional object that contains cells into sections and mounting the sections onto a planar surface, i.e., producing a tissue section, absorbing the cellular components onto the surface that is functionalized with affinity agents (e.g. antibodies, haptens, nucleic acid probes), introducing the biomolecules into a polymer gel or transferring them onto a polymer surface electrophoretically or by other means. The cells or biomolecules may be fixed using any number of reagents including formalin, methanol, paraformaldehyde, methanol:acetic acid, glutaraldehyde, bifunctional cross-linkers such as bis(succinimidyl)suberate, bis(succinimidyl) polyethyleneglycole etc. This definition is intended to cover cellular samples (e.g., tissue sections, etc.), electrophoresis gels and blots thereof, Western blots, dot-blots, ELISAs, antibody microarrays, nucleic acid microarrays, etc.

As used herein, the term "tissue section" refers to a piece of tissue that has been obtained from a subject, fixed, sectioned, and mounted on a planar surface, e.g., a microscope slide.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a microscope slide.

As used herein, the term "non-planar sample" refers to a sample that is not substantially flat, e.g., a whole or part organ mount (e.g., of a lymph node, brain, liver, etc.), that has been made transparent by means of a refractive index matching technique such as Clear Lipid-exchanged Acrylamide-hybridized Rigid Imaging-compatible Tissue-hydrogel (CLARITY). See, e.g., Roberts et al., J Vis Exp. 2016; (112): 54025. Clearing agents such as Benzyl-Alcohol/ Benzyl Benzoate (BABB) or Benzyl-ether may be used to render a specimen transparent.

As used herein, the term "spatially-addressable measurements" refers to a set of values that are each associated with a specific position on a surface. Spatially-addressable measurements can be mapped to a position in a sample and can be used to reconstruct an image, e.g., a two- or three-dimensional image,of the sample.

A "diagnostic marker" is a specific biochemical in the body which has a particular molecular feature that makes it useful for detecting a disease, measuring the progress of disease or the effects of treatment, or for measuring a process of interest.

A "pathoindicative" cell is a cell which, when present in a tissue, indicates that the animal in which the tissue is located (or from which the tissue was obtained) is afflicted with a disease or disorder. By way of example, the presence of one or more breast cells in a lung tissue of an animal is an indication that the animal is afflicted with metastatic breast cancer.

The term "complementary site" is used to refer to an epitope for an antibody or aptamer. Specifically, if the capture agent is an antibody or aptamer, then the complementary site for the capture agent is the epitope in the sample to which the antibody binds.

The term "epitope" as used herein is defined as a small chemical group on the antigen molecule that is bound to by an antibody or aptamer. An antigen can have one or more epitopes. In many cases, an epitope is roughly five amino acids or sugars in size. One skilled in the art understands that generally the overall three-dimensional structure or the specific linear sequence of the molecule can be the main criterion of antigenic specificity.

A "subject" of diagnosis or treatment is a plant or animal, including a human. Non-human animals subject to diagnosis or treatment include, for example, livestock and pets.

As used herein, the term "incubating" refers to maintaining a sample and capture agent under conditions (which conditions include a period of time, a temperature, an appropriate binding buffer and a wash) that are suitable for specific binding of the capture agent to molecules (e.g., epitopes or complementary nucleic acid) in the sample.

As used herein, the term "capture agent" refers to an agent that can specifically bind to complementary sites in a sample. Exemplary capture agents include antibodies and aptamers. If antibodies or aptamers are used, in many cases they may bind to protein epitopes.

As used herein, the term "capture agent that is linked to a oligonucleotide" refers to a capture agent, e.g., an antibody or aptamer, that is non-covalently (e.g., via a streptavidin/ biotin interaction) or covalently (e.g., via a click reaction or the like) linked to a single-stranded oligonucleotide in a way that the capture agent can still bind to its binding site. The nucleic acid and the capture agent may be linked via a number of different methods, including those that use maleimide or halogen-containing group, which are cysteine-reactive. The capture agent and the oligonucleotide may be linked proximal to or at the 5' end of the oligonucleotide, proximal to or at the 3' end of the oligonucleotide, or anywhere in-between.

As used herein, the term "removing", in the context of removing the labels and/or the probes that are associated with, i.e., hybridized to, a sample, refers to any method for physically separatinging the labels and/or probes from a sample. The labels and/or the probes can be removed from the sample by denaturation or by cleaving a linkage in the probe or a linker that attaches the label to the probe, for example, where the removal method used leaves the unhybridized oligonucleotides that are attached to the other antibodies intact and free to hybridize to the labeled probes used in the next cycle.

As used herein, the term "inactivating", in the context of inactivating a label, refers to chemically modifying a label so that it no longer produces a detectable signal. Photobleaching is one way to inactivate a label, although other ways are known.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides, ribonucleotides or a combination thereof, and may be produced enzymatically or synthetically (e.g., PNA as described in U.S. Pat No. 5,948,902 and the references cited therein) and which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as an inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

As used herein, the term "oligonucleotide" refers to a multimer of at least 10, e.g., at least 15 or at least 30 nucleotides. In some embodiments, an oligonucleotide may be in the range of 15-200 nucleotides in length, or more. Any oligonucleotide used herein may be composed of G, A, T and C, or bases that are capable of base pairing reliably with a complementary nucleotide. 7-deaza-adenine, 7-deaza-guanine, adenine, guanine, cytosine, thymine, uracil, 2-deaza-2-thio-guanosine, 2-thio-7-deaza-guanosine, 2-thio-adenine, 2-thio-7-deaza-adenine, isoguanine, 7-deaza-guanine, 5,6-dihydrouridine, 5,6-dihydrothymine, xanthine, 7-deaza-xanthine, hypoxanthine, 7-deaza-xanthine, 2,6 diamino-7-deaza purine, 5-methyl-cytosine, 5-propynyl-uridine, 5-propynyl-cytidine, 2-thio-thymine or 2-thio-uridine are examples of such bases, although many others are known. As noted above, an oligonucleotide may be an LNA, a PNA, a UNA, or an morpholino oligomer, for example. The oligonucleotides used herein may contain natural or non-natural nucleotides or linkages.

As used herein, the term "reading" in the context of reading a fluorescent signal, refers to obtaining an image by scanning or by microscopy, where the image shows the pattern of fluorescence as well as the intensity of fluorescence in a field of view.

As used herein, the term "signal generated by", in the context of reading a fluorescent signal generated by addition of the fluorescent nucleotide, refers to a signal that is emitted directly from the fluorescent nucleotide, a signal that is emitted indirectly via energy transfer to another fluorescent nucleotide (i.e., by FRET). For example, in some embodiments, the method may be implemented using a molecular inversion probe with a donor fluor at one end and an acceptor fluor at the other for fluorescence energy transfer. When the probe is free in solution the two fluors are far apart. When they are hybridized to the oligo on the antibody, the two fluors are immediately adjacent to each other.

Other definitions of terms may appear throughout the specification.

DETAILED DESCRIPTION

A method for analyzing a sample, e.g., a planar sample, is provided. In some embodiments, the method may comprise obtaining: i. a plurality of capture agents that are each linked to a different oligonucleotide and ii. a corresponding plurality of labeled nucleic acid probes (where the term "corresponding" is intended to mean that the number of labeled nucleic acid probes is the same as the number of capture agents used), where each of the labeled nucleic acid probes is complementary to and specifically hybridizes with only one of the oligonucleotides. For example, if there are 50 capture agents then they are each linked to different oligonucleotides and there are 50 labeled nucleic acid probes, where each labeled nucleic acid probe is complementary to and specifically hybridizes with only one of the oligonucleotides. The number of capture agents and labeled nucleic acid probes used in the method may vary. In some embodiments, the method may be performed using: i. at least 10 or at least 20 and up to 50 or 100 or more capture agents, each linked to a different oligonucleotide, and ii. a corresponding number of labeled nucleic acid probes.

In some embodiments, the method may comprise labeling the sample with the plurality of capture agents. This step involves contacting the sample (e.g., an FFPE section mounted on a planar surface such as a microscope slide) with all of the capture agents, en masse under conditions by which the capture agents bind to complementary sites in (e.g., protein epitopes) in the sample. Methods for binding antibodies and aptamers to sites in the sample are well known. In some embodiments, the capture agents may be cross-linked to the sample, thereby preventing the capture agent from disassociating during subsequent steps. This crosslinking step may be done using any amine-to-amine crosslinker (e.g. formaldehyde, disuccinimiyllutarate or another reagent of similar action) although a variety of other chemistries can be used to cross-link the capture agent to the sample if desired.

After the sample has been bound to the capture agents, the method may involve specifically hybridizing a first sub-set of the labeled nucleic acid probes with the sample, wherein the probes in the first sub-set are distinguishably labeled, to produce labeled probe/oligonucleotide duplexes. By "sub-set" is meant at least two, e.g., two, three or four and the term "distinguishably labeled" means that the labels can be separately detected, even if they are at the same location. As such, in some embodiments, the method may involve specifically hybridizing two, three or four of the labeled nucleic acid probes with the sample, thereby producing labeled probe/oligonucleotide duplexes that are linked to antibodies that are bound to sites in the sample. The label may be a pro-fluorophore, a secondary activatible fluorophore, a fluorescent protein, a visible stain, a polychromatic barcode, a mass tag (e.g., an isotope or a polymer of a defined size), a structural tags for label-free detection, a radio sensitive tag (activated by THz camera) a radioactive tag or an absorbance tag that only absorbs light at a specific frequency for example. In some embodiments, an oligonucleotide may deliver an enzyme that delivers a fluorophore or there may be an enzymatic amplification of signal. In some embodiments, the signal detected may be generated by fluorescence resonance energy transfer (FRET) and in other embodiments the detection may be done by raman spectroscopy, infrared detection, or magnetic/electrical detection. In some embodiments, the detecting step may involve a secondary nucleic acid amplification step, including, but not limited, to hybridization chain reaction, branched DNA (bDNA) amplification, etc.

Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 and TOPRO3 (Molecular Probes, Eugene, Oreg.). Further suitable distinguishable detectable labels may be found in Kricka et al. (Ann Clin Biochem. 39:114-29, 2002), Ried et al. (Proc. Natl. Acad. Sci. 1992: 89: 1388-1392) and Tanke et al. (Eur. J. Hum. Genet. 1999 7:2-11) and others. In some embodiments three or four distinguishable dyes may be used. Specific fluorescent dyes of interest include: xanthene dyes, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2', 7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g., Cy3, Cy5 and Cy7 dyes; coumarins, e.g., umbelliferone; benzimide dyes, e.g. Hoechst 33258; phenanthridine dyes, e.g., Texas Red; ethidium dyes; acridine dyes; carbazole dyes; phenoxazine dyes; porphyrin dyes; polymethine dyes, e.g., BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, Napthofluorescein, Texas Red, Cy3, and Cy5, etc. As noted above, within each sub-set of probes, the fluorophores may be chosen so that they are distinguishable, i.e., independently detectable, from one another, meaning that the labels can be independently detected and measured, even when the labels are mixed. In other words, the amounts of label present (e.g., the amount of fluorescence) for each of the labels are separately determinable, even when the labels are co-located (e.g., in the same tube or in the same area of the section).

After the sample has been washed to remove labeled nucleic acid probes that have not hybridized, the method comprises reading the sample to obtain an image showing the binding pattern for each of the sub-set of probes hybridized in the prior step. This step may be done using any convenient reading method and, in some embodiments, e.g., hybridization of the different probes can be separately read using a fluorescence microscope equipped with an appropriate filter for each fluorophore, or by using dual or triple band-pass filter sets to observe multiple fluorophores (see, e.g., U.S. Pat. No. 5,776,688).

After reading the sample, the method may comprise inactivating or removing the labels that are associated with (i.e., hybridized to) the sample, leaving the plurality of capture agents and their associated oligonucleotides (i.e., the unhybridized oligonucleotides) still bound to the sample. The labels that are associated the sample may be removed or inactivated by a variety of methods including, but not limited to, denaturation (in which case the label and the probe in its entirety may be released and can be washed away), by cleaving a linkage in the probe (in which case the label and part of the probe may be released and can be washed away), by cleaving both the probe and the oligonucleotide to which the probe is hybridized (to release a fragment that can be washed away), by cleaving the linkage between the probe and the label (in which case the label will be released and can be washed away and can be washed away), or by inactivating the label itself (e.g., by breaking a bond in the label, thereby preventing the label from producing a signal). In all of these removal methods, the unhybridized oligonucleotides that are attached to the other antibodies are intact and free to hybridize to the set of labeled probes used in the next cycle. In some embodiments, fluorescence may be inactivated by peroxide-based bleaching or cleavage of a fluorophore linked to a nucleotide through a cleavable linker (e.g. using TCEP as a cleaving reagent).

In some embodiments, the removing step is done by removing the hybridized probes from the sample by denaturation, leaving the other capture agents (i.e., the capture agents that are not hybridized to a probe) and their associated oligonucleotides still bound to the sample. In other embodiments, the removing step is not done by removing the hybridized probes from the sample by denaturation, leaving the other capture agents (i.e., the capture agents that are not hybridized to a probe) and their associated oligonucleotides still bound to the sample. In these embodiments, the labels may be removed by cleaving at least one bond in the probes that are associated with the sample, or a linker that links the probes to the labels, thereby releasing the labels from the probes. This cleavage can be done enzymatically, chemically or via exposure to light. Alternatively, the labels can be inactivated by photobleaching or by chemically altering the label).

If removal step is not done by removing the hybridized probes from the sample by denaturation, then a variety of chemical-based, enzyme-catalyzed or photo-induced cleavage methods may be used. For example, in some embodiments, the probes may contain a chemically or photo-cleavable linkage so that they can be fragmented by exposure to a chemical or light. In some embodiments, the duplexes (because they are double stranded) may be cleaved by a restriction enzyme or a double-stranded DNA specific endonuclease (a fragmentase), for example. In some embodiments, the probe may contain a uracil (which can be cleaved by USER), or may contain a hairpin that contains a mismatch, which can be cleaved using a mismatch-specific endonuclease. In some of these embodiments, after cleavage the Tm of the fragment of the probe that contains the label may be insufficiently high to remain base paired with the oligonucleotide and, as such, the fragment will disassociate from the oligonucleotide. In some embodiments, the probe and the label may be connected by a photo-cleavable or chemically-cleavable linker. Cleavage of this linker will release the label from the sample. In other embodiments, the probe may be an RNA, and the probe can be degraded using an RNAse. In some embodiments, an enzymatically cleavable linkage can be used. For example, esters can be cleaved by an esterase and a glycan can be cleated by a glycases. Alternatively the label itself may be inactivated by modifying the label. In one example, the dye may be photobleached, but other methods are known.

In some embodiments, after reading the sample, the method may comprise (e) removing the probes hybridized in step (c) from the sample by denaturation (i.e., by un-annealing the labeled probes from the oligonucleotides and washing them away), leaving the capture agents of (b) and their associated oligonucleotides still bound to the sample. This step may be done using any suitable chemical denaturant, e.g., formamide, DMSO, urea, or a chaotropic agent (e.g., guanidinium chloride or the like), using a toehold release strategy (see, e.g., Kennedy-Darling, Chembiochem. 2014 15: 2353-2356), or using heat, base, a topoisomerase or a single-strand binding agent (e.g., SSBP). This step can also be achieved through hybridization of an oligonucleotide with a greater affinity (e.g. PNA). In some cases, the probes may by removed by incubating the sample in 70% to 90% formamide (e.g., 75% to 85% formamide) for a period of at least 1 minute (e.g., 1 to 5 mins), followed by a wash. This denaturation step may be repeated, if necessary, so that all of the hybridized probes have been removed. As would be apparent, this step is not implemented enzymatically, i.e., does not use a nuclease such as a DNAse or a restriction enzyme, and does not result in cleavage of any covalent bonds, e.g., in any of the probes or oligonucleotides or removal of any of the capture agents from the sample. In this step, the strands of the probe/oligonucleotide duplexes are separated from one another (i.e., denatured), and the separated probes, which are now free in solution, are washed away, leaving the capture agents and their associated oligonucleotides intact and in place.

If a cleavable linkage is used (e.g., in the probes or to connect the probes to the labels, then the cleavable linker should be capable of being selectively cleaved using a stimulus (e.g., light or a change in its environment) without breakage of bonds in the oligonucleotides attached to the antibodies. In some embodiments, the cleavable linkage may be a disulfide bond, which can be readily broken using a reducing agent (e.g., β-mercaptoethanol or the like). Suitable cleavable bonds that may be employed include, but are not limited to, the following: base-cleavable sites such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable sites such as benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable sites such as phthalamide (cleavable by substituted hydrazines), esters (cleavable by, for example, aluminum trichloride); and Weinreb amide (cleavable by lithium aluminum hydride); and other types of chemically cleavable sites, including phosphorothioate (cleavable by silver or mercuric ions) and diisopropyldialkoxysilyl (cleavable by fluoride ions). Other cleavable bonds will be apparent to those skilled in the art or are described in the pertinent literature and texts (e.g., Brown (1997) Contemporary Organic Synthesis 4(3); 216-237). A cleavable bond may be cleaved by an enzyme in some embodiments, In particular embodiments, a photocleavable ("PC") linker (e.g., a uv-cleavable linker) may be employed. Suitable photocleavable linkers for use may include ortho-nitrobenzyl-based linkers, phenacyl linkers, alkoxybenzoin linkers, chromium arene complex linkers, NpSSMpact linkers and pivaloylglycol linkers, as described in Guillier et al (Chem Rev. 2000 Jun. 14; 100(6):2091-158). Exemplary linking groups that may be employed in the subject methods may be described in Guillier et al, supra and Olejnik et al. (Methods in Enzymology 1998 291:135-154), and further described in U.S. Pat. No. 6,027,890; Olejnik et al. (Proc. Natl. Acad Sci, 92:7590-94); Ogata et al. (Anal. Chem. 2002 74:4702-4708); Bai et al. (Nucl. Acids Res. 2004 32:535-541); Zhao et al. (Anal. Chem. 2002 74:4259-4268); and Sanford et al. (Chem Mater. 1998 10:1510-20), and are purchasable from Ambergen (Boston, Mass.; NHS-PC-LC-Biotin), Link Technologies (Bellshill, Scotland), Fisher Scientific (Pittsburgh, Pa.) and Calbiochem-Novabiochem Corp. (La Jolla, Calif.).

After removal of the probes, the sample may be hybridized with a different sub-set of the labeled probes (e.g., a second sub-set of two to four of the labeled probes, where the probes are distinguishably labeled), and the sample may be re-read to produce an image showing the binding pattern for each of the most recently hybridized sub-set of probes. After thet sample has been read, the probes may be removed from the sample, e.g., by denaturation or another method (as described above), and the hybridization and reading steps may be repeated with a different sub-set of distinguishably labeled probes. In other words, the method may comprise repeating the hybridization, label removal or inactivation and reading steps multiple times with a different sub-set of two to four of the labeled nucleic acid probes, where the probes in each sub-set are distinguishably labeled and each repeat is followed by removal of the probes, e.g., by denaturation or another method (except for the final repeat) to produce a plurality of images of the sample, where each image corresponds to a sub-set of labeled nucleic acid probes. The hybridization/reading/label removal or inactivation steps can be repeated until all of the probes have been analyzed.

As would be apparent, the DNA sequences used may be selected in order to minimize background staining, either from non-specific adsorption or through binding to endogenous genomic sequences (RNA or DNA). Likewise, the hybridization and washing buffers may be designed to minimize background staining either from non-specific adsorption or through binding to endogenous genomic sequences (RNA or DNA) or through binding to other reporter sequences In some embodiments, after labeling the sample with the capture agents, the method may comprise: specifically hybridizing a first sub-set of the labeled nucleic acid probeswith the sample, wherein the probes in the first sub-set are distinguishably labeled, to produce labeled probe/oligonucleotide duplexes; reading the sample to obtain an image showing the binding pattern for each of the probes hybridized in the prior step; removing the probes hybridized in the prior step from the sample, by denaturation or another method, leaving the plurality of capture agents and their associated oligonucleotides still bound to the sample; specifically hybridizing a second sub-set of the labeled nucleic acid probes with the sample, wherein the probes in the second sub-set are distinguishably labeled, to produce labeled probe/oligonucleotide duplexes; reading the sample to obtain an image showing the binding pattern for each of the probes in the second sub-set of probes; removing the probes in the probes in the second sub-set that are hybridized to the sample, by denaturation or another methodmethod, leaving the plurality of capture agents and their associated oligonucleotides still bound to the sample. The hybridization/reading/label removal or inactivation cycle can then be repeated for a third, fourth and fifth or more sub-set of probes until all of the probes have been hybridized and read, with the exception that in the final cycle the probes do not need to be removed from the sample. In some cases, the hybridization/reading steps may be repeated 2 to 20 or more times, with a denaturation step after each reading except for the last repeat.

In some embodiments, the labeled nucleic acid probes are 8 to 20 nucleotides in length, e.g., 10 to 18 nucleotides or 11 to 17 nucleotides in length although, in some embodiments, the probe may be as short as 5 nucleotides in length to as long as a 150 nucleotides in length (e.g., 6 nucleotides in length to 100 nucleotides in length). In some embodiments, a probe may have a calculated Tm in the range of 15° C. to 70° C. (e.g., 20° C.-60° C. or 35° C.-50° C.) such that the duplexes of the hybridization step have a Tm in the same range. In these embodiments, the Tm may be calculated using the IDT oligoanalyzer program (available at IDT's website and described in Owczarzy et al., Nucleic Acids Res. 2008 36: W163-9) using default settings of 50 mM Na+, 250 nM oligonucleotide. The sequence of the probes can be any sequence although, in some embodiments, each labeled nucleic acid probe may have a sequence selected from SEQ ID NOS: 1-47, or a complement thereof. In some embodiments, the probes are $T_m$-matched, where the term "$T_m$-matched" refers to sequences that have melting temperatures that are within a defined range, e.g., less than 15° C., less than 10° C. or less than 5° C. of a defined temperature. As would be apparent, the probes may be labeled at the 5' end, the 3' end or anywhere in between. In some embodiments, the probes may be specifically cleavable, e.g., may contain a cleavable linker (e.g., a photo- or chemically-cleavable linker). Likewise, the oligonucleotides may be at least 5 nucleotides in length, e.g., at least 10, at least 15 or at least 20 such as 30-40 nucleotides in length.

In some embodiments, the sequences of the oligonucleotides to which the capture agents are linked are the same length and are perfectly complementary to the labeled probes. In these embodiments, the oligonucleotides may be linked to the capture agents by a linker that spaces the oligonucleotide from the capture agents. In other embodiments, the sequences of the oligonucleotides to which the capture agents are linked are: i. longer than the sequences of the labeled nucleic acid probes and otherwise identical to one other except for a sub-sequence that is complementary to a single labeled nucleic acid probe. In these embodiments, the extra sequence acts as a linker to space the oligonucleotides from the capture agents. In certain embodiment, the oligonucleotides that are linked to the capture agents are from 38 to 40 nt in length. Oligonucleotides may be linked to capture agents using any convenient method (see, e.g., Gong et al., Bioconjugate Chem. 2016 27: 217-225 and Kazane et al. Proc Natl Acad Sci 2012 109: 3731-3736). A variety of labeling methods are available. For example, the unique oligonucleotides may be linked to the capture agents directly using any suitable chemical moiety on the capture agent (e.g., a cysteine residue or via an engineered site). In other embodiments, a common oligonucleotide may be conjugated directly to all of the capture agent using any suitable chemistry, and the unique oligonucleotides may be linked to the common oligonucleotides enzymatically, e.g., by ligation. In other embodiments, the unique oligonucleotides may be linked to the capture agents directly or indirectly via a non-covalent interaction, e.g., via a biotin/streptavidin or an equivalent thereof, via an aptamer or secondary antibody, or via a protein-protein interaction such as a leucine-zipper tag interaction or the like. In alternative embodiments, the oligonucleotides and probes of the present method can be substituted for other entities that can bind to one another in a specific manner, e.g., leucine zipper pairs or antigen/antibody pairs.

Each reading step produces an image of the sample showing the pattern of binding of a sub-set of probes. In some embodiments, the method may further comprise analyzing, comparing or overlaying, at least two of the images. In some embodiments, the method may further comprise overlaying all of the images to produce an image showing the pattern of binding of all of the capture agents to the sample. The image analysis module used may transform the signals from each fluorophore to produce a plurality of false color images. The image analysis module may overlay the plurality of false color images (e.g., superimpose the false colors at each pixel) to obtain a multiplexed false color image. Multiple images (e.g., unweighted or weighted) may be transformed into a single false color, e.g., so as to represent a biological feature of interest characterized by the binding of specific capture agent. False colors may be assigned to specific capture agents or combinations of capture agents, based on manual input from the user. In certain aspects, the image may comprise false colors relating only to the intensities of labels associated with a feature of interest, such as in the nuclear compartment. The image analysis module may further be configured to adjust (e.g., normalize) the intensity and/or contrast of signal intensities or false colors, to perform a convolution operation (such as blurring or sharpening of the intensities or false colors), or perform any other suitable operations to enhance the image. The image analysis module may perform any of the above operations to align pixels obtained from successive images and/or to blur or smooth intensities or false colors across pixels obtained from successive images.

In some embodiments, images of the sample may be taken at different focal planes, in the z direction. These optical sections can be used to reconstruct a three dimensional image of the sample. Optical sections may be taken using confocal microscopy, although other methods are known. The image analysis method may be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into a memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer, which runs the program, and returns an output to the user.

In addition to the labeling methods described above, the sample may be stained using a cytological stain, either before or after performing the method described above. In these embodiments, the stain may be, for example, phalloidin, gadodiamide, acridine orange, bismarck brown, barmine, Coomassie blue, bresyl violet, brystal violet, DAPI, hematoxylin, eosin, ethidium bromide, acid fuchsine, haematoxylin, hoechst stains, iodine, malachite green, methyl green, methylene blue, neutral red, Nile blue, Nile red, osmium tetroxide (formal name: osmium tetraoxide), rhodamine, safranin, phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, vanadyl sulfate, or any derivative thereof. The stain may be specific for any feature of interest, such as a protein or class of proteins, phospholipids, DNA (e.g., dsDNA, ssDNA), RNA, an organelle (e.g., cell membrane, mitochondria, endoplasmic recticulum, golgi body, nuclear envelope, and so forth), or a compartment of the cell (e.g., cytosol, nuclear fraction, and so forth). The stain may enhance contrast or imaging of intracellular or extracellular structures. In some embodiments, the sample may be stained with haematoxylin and eosin (H&E).

Kits

Also provided by this disclosure are kits that contain reagents for practicing the subject methods, as described above. In some embodiments, the kit may comprise a first population of at least 10 oligonucleotides (e.g., at least 15, at least 20, at least 30, at least 40 or all 47) wherein the sequences of said at least 10 oligonucleotides consist of sequences selected from SEQ ID NOS: 1-47, or complements thereof. In many embodiments, these oligonucleotides are in an aqueous solution and are not tethered to solid support. In some embodiments, the oligonucleotides are labeled (e.g., linked to a fluorophore) but in other embodiments they are not labeled. These oligonucleotides may be in separate vessels or mixed in the same vessel. In some embodiments, the oligonucleotides are in mixtures comprising up to 3 of said oligonucleotides, where the oligonucleotides are distinguishably labeled. In some embodiments, the kit may contain a second population of oligonucleotides, wherein the oligonucleotides in the second population each comprise a sequence that is complementary to the full length of an oligonucleotide in the first population. In these embodiments, the oligonucleotides in the second population may be each linked to a capture agent. In some embodiments, the oligonucleotides in the second population may be longer than the oligonucleotides in the first population. The various components of the kit may be present in separate containers or certain compatible components may be pre-combined into a single container, as desired. In some embodiments, the probes used may contain a cleavable linkage (e.g., a chemically or photo-cleavable linkage).

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Systems

Aspects of the invention include systems and devices thereof configured for analyzing a sample. In some embodiments, the subject systems include a sample well, an autosampler, a controller, a processor, and a computer-readable medium comprising instructions that, when executed by the processor, cause the controller to analyze the sample. Each of these components is now further described in greater detail.

In some embodiments, the system includes a sample well, and each cycle of analysis involves delivery of three types of solution to the sample well: 1) oligonucleotide mix, 2) wash solution and 3) formamide solution. In some embodiments, for ease of use and reproducibility purposes, the fluidics is fully automated. In certain embodiments, an autosampler is programmed in line with a series of pumps controlling each solution.

As summarized above, aspects of the invention include a controller, processor and computer readable medium that are configured or adapted to control or operate one or more components of the subject systems. In some embodiments, a system includes a controller that is in communication with one or more components of the systems, as described herein, and is configured to control aspects of the systems and/or execute one or more operations or functions of the subject systems. In some embodiments, a system includes a processor and a computer-readable medium, which may include memory media and/or storage media. Applications and/or operating systems embodied as computer-readable instructions on computer-readable memory can be executed by the processor to provide some or all of the functionalities described herein. In certain embodiments, the entire set of commands to complete a single analysis cycle is fully automated and controlled by a python program.

In some embodiments, a system includes a user interface, such as a graphical user interface (GUI), that is adapted or configured to receive input from a user, and to execute one or more of the methods as described herein. In some embodiments, a GUI is configured to display data or information to a user.

Utility

The methods and compositions described herein find general use in a wide variety of applications for analysis of any sample (e.g., in the analysis of tissue sections, sheets of cells, spun-down cells, blots of electrophoresis gels, Western blots, dot-blots, ELISAs, antibody microarrays, nucleic acid microarrays, whole tissues or parts thereof, etc.). The method may be used to analyze any tissue, including tissue that has been clarified, e.g., through lipid elimination, for example. The sample may be prepared using expansion microscopy methods (see, e.g., Chozinski et al. Nature Methods 2016 13: 485-488), which involves creating polymer replicas of a biological system created through selective co-polymerization of organic polymer and cell components. The method can be usedused to analyze spreads of cells, exosomes, extracellular structures, biomolecules deposited on a solid support or in a gel (Elisa, western blot, dot blot), whole organism, individual organs, tissues, cells, extracellular components, organelles, cellular components, chromatin and epigenetic markers, biomolecules and biomolecular complexes, for example. The capture agents may bind to any type of molecule, including proteins, lipids, polysaccharides, proteoglycans, metabolites, or artificial small molecules or the like. The method may have many biomedical applications in high throughput screening and drug discovery and the like. Further, the method has a variety of clinical applications, including, but not limited to, diagnostics, prognostics, disease stratification, personalized medicine, clinical trials and drug accompanying tests.

In particular embodiments, the sample may be a section of a tissue biopsy obtained from a patient. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc.

In certain embodiments, capture agents specifically bind to biomarkers, including cancer biomarkers, that may be proteinaceous. Exemplary cancer biomarkers, include, but are not limited to carcinoembryonic antigen (for identification of adenocarcinomas), cytokeratins (for identification of carcinomas but may also be expressed in some sarcomas), CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumour identification), CD20 (for identification of B-cell lymphomas) and CD3 (for identification of T-cell lymphomas).

The above-described method can be used to analyze cells from a subject to determine, for example, whether the cell is normal or not or to determine whether the cells are responding to a treatment. In one embodiment, the method may be employed to determine the degree of dysplasia in cancer cells. In these embodiments, the cells may be a sample from a multicellular organism. A biological sample may be isolated from an individual, e.g., from a soft tissue. In particular cases, the method may be used to distinguish different types of cancer cells in FFPE samples.

The method described above finds particular utility in examining samples using a plurality of antibodies, each antibodyy recognizing a different marker. Examples of cancers, and biomarkers that can be used to identify those cancers, are shown below. In these embodiments, one does not need to examine all of the markers listed below in order to make a diagnosis.

In some embodiments, the method may involve obtaining an image as described above (an electronic form of which may have been forwarded from a remote location), and the image may be analyzed by a doctor or other medical professional to determine whether a patient has abnormal cells (e.g., cancerous cells) or which type of abnormal cells are present. The image may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

The compositions and methods described herein can be used to diagnose a patient with a disease. In some cases, the presence or absence of a biomarker in the patient's sample can indicate that the patient has a particular disease (e.g., cancer). In some cases, a patient can be diagnosed with a disease by comparing a sample from the patient with a sample from a healthy control. In this example, a level of a biomarker, relative to the control, can be measured. A difference in the level of a biomarker in the patient's sample relative to the control can be indicative of disease. In some cases, one or more biomarkers are analyzed in order to diagnose a patient with a disease. The compositions and methods of the disclosure are particularly suitedfor identifying the presence or absence of, or determining expression levels, of a plurality of biomarkers in a sample.

In some cases, the compositions and methods herein can be used to determine a treatment plan for a patient. The

| | |
|---|---|
| Acute Leukemia IHC Panel | CD3, CD7, CD20, CD34, CD45, CD56, CD117, MPO, PAX-5, and TdT. |
| Adenocarcinoma vs. Mesothelioma IHC Panel | Pan-CK, CEA, MOC-31, BerEP4, TTF1, calretinin, and WT-1. |
| Bladder vs. Prostate Carcinoma IHC Panel | CK7, CK20, PSA, CK 903, and p63. |
| Breast IHC Panel | ER, PR, Ki-67, and HER2. Reflex to HER2 FISH after HER2 IHC is available. |
| Burkitt vs. DLBC Lymphoma IHC panel | BCL-2, c-MYC, Ki-67. |
| Carcinoma Unknown Primary Site, Female (CUPS IHC Panel—Female) | CK7, CK20, mammaglobin, ER, TTF1, CEA, CA19-9, S100, synaptophysin, and WT-1. |
| Carcinoma Unknown Primary Site, Male (CUPS IHC Panel—Male) | CK7, CK20, TTF1, PSA, CEA, CA19-9, S100, and synaptophysin. |
| GIST IHC Panel | CD117, DOG-1, CD34, and desmin. |
| Hepatoma/Cholangio vs. Metastatic Carcinoma IHC Panel | HSA (HepPar 1), CDX2, CK7, CK20, CAM 5.2, TTF-1, and CEA (polyclonal). |
| Hodgkin vs. NHL IHC Panel | BOB-1, BCL-6, CD3, CD10, CD15, CD20, CD30, CD45 LCA, CD79a, MUM1, OCT-2, PAX-5, and EBER ISH. |
| Lung Cancer IHC Panel | chromogranin A, synaptophysin, CK7, p63, and TTF-1. |
| Lung vs. Metastatic Breast Carcinoma IHC Panel | TTF1, mammaglobin, GCDFP-15 (BRST-2), and ER. |
| Lymphoma Phenotype IHC Panel | BCL-2, BCL-6, CD3, CD4, CD5, CD7, CD8, CD10, CD15, CD20, CD30, CD79a, CD138, cyclin D1, Ki67, MUM1, PAX-5, TdT, and EBER ISH. |
| Lymphoma vs. Carcinoma IHC Panel | CD30, CD45, CD68, CD117, pan-keratin, MPO, S100, and synaptophysin. |
| Lymphoma vs. Reactive Hyperplasia IHC Panel | BCL-2, BCL-6, CD3, CD5, CD10, CD20, CD23, CD43, cyclin D1, and Ki-67. |
| Melanoma vs. Squamous Cell Carcinoma IHC Panel | CD68, Factor XIIIa, CEA (polyclonal), S-100, melanoma cocktail (HMB-45, MART-1/Melan-A, tyrosinase) and Pan-CK. |
| Mismatch Repair Proteins IHC Panel (MMR/Colon Cancer) | MLH1, MSH2, MSH6, and PMS2. |
| Neuroendocrine Neoplasm IHC Panel | CD56, synaptophysin, chromogranin A, TTF-1, Pan-CK, and CEA (polyclonal). |
| Plasma Cell Neoplasm IHC Panel | CD19, CD20, CD38, CD43, CD56, CD79a, CD138, cyclin D1, EMA, kappa, lambda, and MUM1. |
| Prostate vs. Colon Carcinoma IHC Panel | CDX2, CK 20, CEA (monoclonal), CA19-9, PLAP, CK 7, and PSA. |
| Soft Tissue Tumor IHC Panel | Pan-CK, SMA, desmin, S100, CD34, vimentin, and CD68. |
| T-Cell Lymphoma IHC panel | ALK1, CD2, CD3, CD4, CD5, CD7, CD8, CD10, CD20, CD21, CD30, CD56, TdT, and EBER ISH. |
| T-LGL Leukemia IHC panel | CD3, CD8, granzyme B, and TIA-1. |
| Undifferentiated Tumor IHC Panel | Pan-CK, S100, CD45, and vimentin. | presence or absence of a biomarker may indicate that a patient is responsive to or refractory to a particular therapy. For example, a presence or absence of one or more biomarkers may indicate that a disease is refractory to a specific therapy, and an alternative therapy can be administered. In some cases, a patient is currently receiving the therapy and the presence or absence of one or more biomarkers may indicate that the therapy is no longer effective.

In any embodiment, data can be forwarded to a "remote location", where "remote location," means a location other than the location at which the image is examined For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" informationrefers to transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the image may be analyzed by an MD or other qualified medical professional, and a report based on the results of the analysis of the image may be forwarded to the patient from which the sample was obtained.

In some cases, the method may be employed in a variety of diagnostic, drug discovery, and research applications that include, but are not limited to, diagnosis or monitoring of a disease or condition (where the image identifies a marker for the disease or condition), discovery of drug targets (where the a marker in the image may be targeted for drug therapy), drug screening (where the effects of a drug are monitored by a marker shown in the image), determining drug susceptibility (where drug susceptibility is associated with a marker) and basic research (where is it desirable to measure the differences between cells in a sample).

In certain embodiments, two different samples may be compared using the above methods. The different samples may be composed of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen, etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material contains cells that are susceptible to infection by a pathogen such as a virus, e.g., human immunodeficiency virus (HIV), etc., and the control material contains cells that are resistant to infection by the pathogen. In another embodiment, the sample pair is represented by undifferentiated cells, e.g., stem cells, and differentiated cells.

The images produced by the method may be viewed side-by-side or, in some embodiments, the images may be superimposed or combined. In some cases, the images may be in color, where the colors used in the images may correspond to the labels used.

Cells from any organism, e.g., from bacteria, yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

EMBODIMENTS

Embodiment 1. A method for analyzing a sample, comprising the following steps, performed in order:
 (a) obtaining:
  i. a plurality of capture agents that are each linked to a different oligonucleotide; and
  ii. a corresponding plurality of labeled nucleic acid probes, wherein each of the labeled nucleic acid probes specifically hybridizes with only one of the oligonucleotides of (a)(i);
 (b) labeling a sample with the plurality of capture agents of (a)(i);
 (c) specifically hybridizing a first sub-set of the labeled nucleic acid probes of (a)(ii) with the sample, wherein the probes in the first sub-set are distinguishably labeled, to produce labeled probe/oligonucleotide duplexes;
 (d) reading the sample to obtain an image showing the binding pattern for each of the probes hybridized in step (c);
 (e) inactivating or removing the labels that are associated with the sample in step (c), leaving the plurality of capture agents of (b) and their associated oligonucleotides still bound to the sample; and
 (f) repeating steps (c) and (d) multiple times with a different sub-set of the labeled nucleic acid probes of (a)(ii), each repeat followed by step (e) except for the final repeat, to produce a plurality of images of the sample, each image corresponding to a sub-set of labeled nucleic acid probes used in (c).

Embodiment 2. The method of embodiment 1, wherein the sample is a planar cellular sample.

Embodiment 2A. The method of any prior embodiment, wherein the sample is a planar sample.

Embodiment 2B. The method of any prior embodiment, wherein the sample is a non-planar sample.

Embodiment 3A. The method of any prior embodiment, wherein the oligonucleotide of (a)(i) is at least 5 nucleotides in length.

Embodiment 3B. The method of any prior embodiment, wherein the oligonucleotides of (a)(i) are 30-40 nucleotides in length.

Embodiment 4A. The method of any prior embodiment, wherein the labeled nucleic acid probes of (a)(ii) are at least 5 nucleotides in length. Embodiment 4B. The method of any prior embodiment, wherein the labeled nucleic acid probes of (a)(ii) are 8 to 30 nucleotides in length.

Embodiment 5. The method of any prior embodiment, wherein the sequences of the oligonucleotides to which the capture agents of (a)(i) are linked are: i. longer than the sequences of the labeled nucleic acid probes of (a)(ii) and ii. otherwise identical to one other except for a sub-sequence that is complementary to a single labeled nucleic acid probe of (a)(ii).

Embodiment 6A6A. The method of any prior embodiment, wherein the duplexes of (c) have a $T_m$ of at least 15° C.

Embodiment 6B. The method of any prior embodiment, wherein the duplexes of (c) have a $T_m$ in the range of the 35° C.-75° C.

Embodiment 7. The method of any prior embodiment, wherein the hybridizing of (c) is for a period of time of about 2 minutes.

Embodiment 8. The method of any prior embodiment, wherein each labeled nucleic acid probe has a sequence selected from SEQ ID NOS: 1-47, or a complement thereof.

Embodiment 9. The method of any prior embodiment, wherein each oligonucleotide linked to a capture agent is selected from SEQ ID NOS: 48-94, or a complement thereof.

Embodiment 10. The method of any prior embodiment, wherein the plurality of capture agents is at least 10 capture agents.

Embodiment 11. The method of any prior embodiment, wherein each of the subsets is independently 2 to 4 labeled nucleic acid probes.

Embodiment 12. The method of any prior embodiment, wherein the probes are removed in step (e) using formamide Embodiment 13. The method of any prior embodiment, wherein the probes are removed in step (e) by incubating the sample in 70% to 90% formamide for a period of at least 1 minute, followed by a wash.

Embodiment 14. The method of any prior embodiment, wherein step (f) comprises repeating steps (c) and (d) 2 to 20 times.

Embodiment 15. The method of any prior embodiment, further comprising analyzing at least two of the images.

Embodiment 16. The method of embodiment 15, wherein the analyzing comprises comparing or overlaying at least two of the images.

Embodiment 17. The method of any prior embodiment, further comprising overlaying all of the images to produce an image showing the pattern of binding of all of the capture agents to the sample.

Embodiment 18. The method of any prior embodiment, wherein the labeled nucleic acid probes are fluorescently labeled.

Embodiment 19. The method of any prior embodiment, wherein reading is done by fluorescence microscopy.

Embodiment 20. The method of any prior embodiment, wherein the capture agent is an antibody or aptamer.

Embodiment 21. The method of any prior embodiment, wherein the sample is a formalin-fixed, paraffin-embedded (FFPE) section or a cell spread.

Embodiment 22. The method of any prior claim, wherein step (e) is done by removing the probes hybridized in step (c) from the sample by denaturation, leaving the plurality of capture agents of (b) and their associated oligonucleotides still bound to the sample.

Embodiment 23. The method of any prior embodiment, wherein step (e) is not done by removing the probes hybridized in step (c) from the sample by denaturation, leaving the plurality of capture agents of (b) and their associated oligonucleotides still bound to the sample.

Embodiment 24. The method of embodiment 23, wherein step (e) is done by cleaving at least one bond in the probes that are associated with the sample in step (c), or a linker that links the probes to the labels, thereby releasing the labels from the probes.

Embodiment 25. The method of embodiment 24, wherein the cleaving is done enzymatically, chemically or via exposure to light.

Embodiment 26. The method of embodiment 23, wherein step (e) is done by inactivating the labels.

Embodiment 27. A kit comprising:

a first population of at least 10 nucleic acid probes wherein the sequences of said at least 10 oligonucleotides consist of sequences selected from SEQ ID NOS: 48-94, or complements thereof.

Embodiment 28. The kit of embodiment 27, wherein the oligonucleotides are labeled.

Embodiment 29. The kit of any of embodiments 27-28, wherein the oligonucleotides are in separate vessels.

Embodiment 30. The kit of any of embodiments 27-29, wherein the oligonucleotides are in mixtures comprising up to 3 of said oligonucleotides.

Embodiment 31. The kit of any of embodiments 27-30, further comprising:

a second population of oligonucleotides, wherein the oligonucleotides in the second population each comprise a sequence that is complementary the full length of an oligonucleotide in the first population.

Embodiment 32. The kit of any of embodiments 27-31, wherein the oligonucleotides in the second population are each linked to a capture agent.

Embodiment 33. The kit of any of embodiments 27-32, wherein the oligonucleotides in the second population are longer than the oligonucleotides in the first population.

Embodiment 34. The kit of any of embodiments 27-33, wherein the oligonucleotides in the second population are selected from SEQ ID NOS: 48-94, or a complement thereof.

Embodiment 35. The kit of any of embodiments 27-34, wherein the probes comprise a cleavable linkage that is not a phosphodiester bond.

Embodiment 36. A system for analyzing a sample, comprising a sample well, an auto-sampler, a controller, a processor, and a computer-readable medium comprising instructions that, when executed by the processor, cause the controller to analyze the sample, wherein the analysis comprises:

(a) labeling the sample with a plurality of capture agents;

(b) specifically hybridizing a first sub-set of a plurality of labeled nucleic acid probes with the sample;

(c) reading the sample to obtain an image showing the binding pattern for each of the probes hybridized in step (b);

(d) removing the labels and/or probes hybridized in step (b) from the sample; and (e) repeating steps (b) and (c) multiple times with a different sub-set of the plurality of the labeled nucleic acid probes, each repeat followed by step (d) except for the final repeat.

Embodiment 37. The system of embodiment 36, wherein the hybridizing of (b) is for a period of about 2 minutes.

Embodiment 38. The system of any of embodiments 36-37, wherein thestep (e) comprises repeating steps (b) and (c) 2 to 20 times.

Embodiment 39. The system any of embodiments 36-38, wherein the plurality of capture agents is at least 10 capture agents.

Embodiment 40. The system any of embodiments 36-39, wherein each of the subsets is independently 2 to 4 labeled nucleic acid probes.

Embodiment 41. The system any of embodiments 36-40, wherein the probes are removed in step (d) by denaturation.

Embodiment 40. The system any of embodiment 41, wherein the probes are removed in step (d) by incubating the sample in 70% to 90% formamide for a period of at least 1 minute, followed by a wash.

Embodiment 41. A method for analyzing a sample, comprising the following steps, performed in order: (a) obtaining: i. a plurality of capture agents that are each linked to a different oligonucleotide; and ii. a corresponding plurality of labeled nucleic acid probes, wherein each of the labeled nucleic acid probes specifically hybridizes with only one of the oligonucleotides of (a)(i); (b) labeling the planar sample with the plurality of capture agents of (a)(i); (c) specifically hybridizing a first sub-set of the labeled nucleic acid probes of (a)(ii) with the sample, wherein the probes in the first sub-set are distinguishably labeled, to produce labeled probe/oligonucleotide duplexes; (d) reading the sample to obtain an image showing the binding pattern for each of the probes hybridized in step (c); (e) removing the probes hybridized in step (c) from the sample by denaturation, leaving the capture agents of (b) and their associated oligonucleotides still bound to the sample; and (f) repeating steps (c) and (d) multiple times with a different sub-set of the labeled nucleic acid probes of (a)(ii), each repeat followed by step (e) except for the final repeat, to produce a plurality of images of the sample, each image corresponding to a sub-set of labeled nucleic acid probes used in (c).

Embodiment 42. The method of embodiment 41, wherein the sample is a planar cellular sample.

Embodiment 43. The method of any of embodiments 41-42, wherein the oligonucleotide of (a)(i) is 30-40 nucleotides in length.

Embodiment 44. The method of any of embodiments 41-43, wherein the labeled nucleic acid probes of (a)(ii) are 8 to 30 nucleotides in length.

Embodiment 45. The method of any of embodiments 41-44, wherein the sequences of the oligonucleotides to which the capture agents of (a)(i) are linked are: i. longer than the sequences of the labeled nucleic acid probes of (a)(ii) and ii. otherwise identical to one other except for a sub-sequence that is complementary to a single labeled nucleic acid probe of (a)(ii).

Embodiment 46. The method of any of embodiments 41-45, wherein the duplexes of (c) have a $T_m$ in the range of the 35° C.-75° C.

Embodiment 47. The method of any of embodiments 41-46, wherein the hybridizing of (c) is for a period of time of about 2 minutes.

Embodiment 48. The method of any of embodiments 41-47, wherein each labeled nucleic acid probe has a sequence selected from SEQ ID NOS: 1-47, or a complement thereof.

Embodiment 49. The method of any of embodiments 41-48, wherein each oligonucleotide linked to a capture agent is selected from SEQ ID NOS: 48-94, or a complement thereof.

Embodiment 50. The method of any of embodiments 41-49, wherein the plurality of capture agents is at least 10 capture agents.

Embodiment 51. The method of any of embodiments 41-50, wherein each of the subsets is independently 2 to 4 labeled nucleic acid probes.

Embodiment 52. The method of any of embodiments 41-51, wherein the probes are removed in step (e) using formamide Embodiment 53. The method of any of embodiments 41-52, wherein the probes are removed in step (e) by incubating the sample in 70% to 90% formamide for a period of at least 1 minute, followed by a wash.

Embodiment 54. The method of any of embodiments 41-53, wherein step (f) comprises repeating steps (c) and (d) 2 to 20 times.

Embodiment 55. The method of any of embodiments 41-54, further comprising analyzing at least two of the images.

Embodiment 56. The method of embodiment 55, wherein the analyzing comprises comparing or overlaying at least two of the images.

Embodiment 57. The method of any of embodiments 41-56, further comprising overlaying all of the images to produce an image showing the pattern of binding of all of the capture agent to the planar sample.

Embodiment 58. The method of any of embodiments 41-57, wherein the labeled nucleic acid probes are fluorescently labeled.

Embodiment 59. The method of any of embodiments 41-58, wherein reading is done by fluorescence microscopy.

Embodiment 60. The method of any of embodiments 41-59, wherein the capture agent is an antibody or aptamer.

Embodiment 61. The method of any of embodiments 41-60, wherein the planar sample is a formalin-fixed, paraffin-embedded (FFPE) section or a cell spread.

In order to further illustrate the present invention, the following specific examples are given with the understanding that they are being offered to illustrate the present invention and should not be construed in any way as limiting its scope.

EXAMPLES

Overall Procedure

Each antibody is conjugated to a unique oligonucleotide, which hybridizes to a shorter complementary oligonucleotide conjugated to a dye molecule. All antibodies are combined, and a target tissue (or cell spread) is stained using this cocktail. The tissue is attached to a flow cell and iterative cycles of oligonucleotide annealing and removal are performed using an auto-sampler to deliver the library of dye-oligonucleotides in sets of three for standard four color microscopes. After each hybridization step, the tissue or cell spread is imaged on a fluorescent microscope. The dye-oligonucleotides are removed using formamide solution in between each cycle. Fluorescent images from each cycle are overlaid and single-cell resolution information is extracted across all cycles and fluorescent channels.

Reagent Design

Oligonucleotide Library

A library of sequence orthogonal oligonucleotide probe sets were designed according to the following criteria: 1) Each probe set contains an oligonucleotide sequence (oligo a) that is between 30-40 nt that is conjugated to an antibody and a complementary oligonucleotide, shorter in length (10-20 nt) that is conjugated to a fluorescent dye (oligo b). 2) Each oligo b has a melting temperature (Tm) between 35° C.-50° C. If the Tm is below 35° C., oligo b does not hybridize to oligo a for the duration of imaging. If the Tm is above 75° C., the dye-oligonucleotide (b) cannot be removed during the formamide incubation step.

The probe set library was screened for sequence overlap. The following sequences were found to have no sequence similarity.

| pair | dye-labeled oligonucleotide (5'-3') (b) | SEQ ID NO. | antibody conjugated oligonucleotide (5'-3') (a) | SEQ ID NO. |
|---|---|---|---|---|
| 1 | TTAGACAACTTTAGT | 1 | ATAGCAGTCCAGCGCCCCACTAAAGTTGTCTAA | 48 |
| 2 | CATCAGGATTTGGTA | 2 | ATAGCAGTCCAGAACGACTACCAAATCCTGATG | 49 |
| 3 | CGCTCCTCATGATAA | 3 | ATAGCAGTCCAGCTATTATCATGAGGAGCGGCG | 50 |
| 4 | CGGCCATCCATTA | 4 | ATAGCAGTCCAGGATCTTAATGGATGGCCGCAG | 51 |
| 5 | GGCTGATTACCCTCT | 5 | ATAGCAGTCCAGCGGGTGAGAGGGTAATCAGCC | 52 |
| 6 | TAGCATTGTGTAGGT | 6 | ATAGCAGTCCAGGTGTCCACCTACACAATGCTA | 53 |
| 7 | GAATCTTATAGAATCGC | 7 | ATAGCAGTCCAGTCGGGCGATTCTATAAGATTC | 54 |
| 8 | CTTATAAGTAGACGC | 8 | ATAGCAGTCCAGCGCATTGCGTCTACTTATAAG | 55 |
| 9 | CTGGGCGAGATATG | 9 | ATAGCAGTCCAGTTAAACGCATATCTCGCCCAG | 56 |
| 10 | CTCGGCCCGAT | 10 | ATAGCAGTCCAGTCATTCGTAGATCGGGCCGAG | 57 |
| 11 | AGATTACTACTCATACA | 11 | ATAGCAGTCCAGTTACTGTATGAGTAGTAATCT | 58 |
| 12 | GCTCTCTGACTTAGA | 12 | ATAGCAGTCCAGGCTACCTCTAAGTCAGAGAGC | 59 |
| 13 | ATCACGGATAATGTC | 13 | ATAGCAGTCCAGGCTCGTGACATTATCCGTGAT | 60 |
| 14 | AGTACTAATAGTAGTGA | 14 | ATAGCAGTCCAGTTTCTCACTACTATTAGTACT | 61 |
| 15 | TGGCATTCTGGC | 15 | ATAGCAGTCCAGCCTTGTTTCGCCAGAATGCCA | 62 |
| 16 | CTCAGGTTCGAGTC | 16 | ATAGCAGTCCAGCTCTTCCGACTCGAACCTGAG | 63 |
| 17 | CTCTGGTAGGATGTA | 17 | ATAGCAGTCCAGTTAGCCTACATCCTACCAGAG | 64 |
| 18 | CACTTTGCCGTGC | 18 | ATAGCAGTCCAGCATGGCCTGCACGGCAAAGTG | 65 |
| 19 | GATACGAGGCGTTAT | 19 | ATAGCAGTCCAGATGGCAATAACGCCTCGTATC | 66 |
| 20 | CACAGACTCCTTTGG | 20 | ATAGCAGTCCAGGAAGCGCCAAAGGAGTCTGTG | 67 |
| 21 | ATTTTCCCGCACG | 21 | ATAGCAGTCCAGTCCGTCTCCGTGCGGGAAAAT | 68 |
| 22 | ATGCAATCACCTGGT | 22 | ATAGCAGTCCAGATACTAACCAGGTGATTGCAT | 69 |
| 23 | GAAGTTTACGGGATA | 23 | ATAGCAGTCCAGGCGCACTATCCCGTAAACTTC | 70 |
| 24 | ACTAAGCGAGTACAC | 24 | ATAGCAGTCCAGGGGCATGTGTACTCGCTTAGT | 71 |
| 25 | AATCTGTTGAAATCA | 25 | ATAGCAGTCCAGGCGGGTGATTTCAACAGATTAA | 72 |
| 26 | GTAGTCCTAAACCAT | 26 | ATAGCAGTCCAGTTGCTGATGGTTTAGGACTACGG | 73 |
| 27 | CGGCGAGGAGTA | 27 | ATAGCAGTCCAGGATAATAGTACTCCTCGCCGCAA | 74 |
| 28 | ACGCCGGTAGGT | 28 | ATAGCAGTCCAGCTAGAATTACCTACCGGCGTCGG | 75 |
| 29 | CCGACTAATGGGAGA | 29 | ATAGCAGTCCAGGCCCACTCTCCCATTAGTCGGAA | 76 |
| 30 | ATCGTAACACATCCA | 30 | ATAGCAGTCCAGCACAGGTGGATGTGTTACGATGG | 77 |
| 31 | CTTAGAATATCTTAGCG | 31 | ATAGCAGTCCAGAGCCCGCTAAGATATTCTAAGTT | 78 |
| 32 | GAATATTCATCTGCG | 32 | ATAGCAGTCCAGGCGTAACGCAGATGAATATTCAA | 79 |

| dye-labeled oligonucleotide pair (5'-3') (b) | SEQ ID NO. | antibody conjugated oligonucleotide (5'-3') (a) | SEQ ID NO. |
|---|---|---|---|
| 33 CTATCGTCCGTGCA | 33 | ATAGCAGTCCAGAATTTGCGTATAGAGCGGGTCAA | 80 |
| 34 GAGCCGGGCTAG | 34 | ATAGCAGTCCAGAGTAAGCATCTAGCCCGGCTCTT | 81 |
| 35 CGAGAGACTGAATCT | 35 | ATAGCAGTCCAGCGATGGAGATTCAGTCTCTCGGG | 82 |
| 36 TAGTGCCTATTACAG | 36 | ATAGCAGTCCAGCGAGCACTGTAATAGGCACTATT | 83 |
| 37 TCATGATTATCATCA | 37 | ATAGCAGTCCAGAAAGAGTGATGATAATCATGAAA | 84 |
| 38 ACCGTAAGACCGCTT | 38 | ATAGCAGTCCAGGGAACAAAGCGGTCTTACGGTTT | 85 |
| 39 GAGTCCAAGCTCAGC | 39 | ATAGCAGTCCAGGAGAAGGCTGAGCTTGGACTCAA | 86 |
| 40 GAGACCATCCTACAT | 40 | ATAGCAGTCCAGAATCGGATGTAGGATGGTCTCGG | 87 |
| 41 GTGAAACGGCACG | 41 | ATAGCAGTCCAGGTACCGGACGTGCCGTTTCACTT | 88 |
| 42 CTATGCTCCGCAATA | 42 | ATAGCAGTCCAGTACCGTTATTGCGGAGCATAGGG | 89 |
| 43 GTGTCTGAGGAAACC | 43 | ATAGCAGTCCAGCTTCGCGGTTTCCTCAGACACGG | 90 |
| 44 TAAAAGGGCGTGC | 44 | ATAGCAGTCCAGAGGCAGAGGCACGCCCTTTTAAA | 91 |
| 45 TACGTTAGTGGACCA | 45 | ATAGCAGTCCAGTATGATTGGTCCACTAACGTAGG | 92 |
| 46 CTTCAAATGCCCTAT | 46 | ATAGCAGTCCAGCGCGTGATAGGGCATTTGAAGGG | 93 |
| 47 TGATTCGCTCATGTG | 47 | ATAGCAGTCCAGCCCGTACACATGAGCGAATCAGG | 94 |

Oligonucleotide Removal

Hybridized dye-labeled oligonucleotides are removed using an 80% formamide solution with 2 mM Tris pH=7.5, 2 mM $MgCl_2$, 25 mM NaCl and 0.02% (v/v) TritonX. In order to completely remove the dye-labeled oligonucleotides during each cycle, three 120-second incubations of the formamide solution on top of the sample followed by 4 washing steps with 10 mM Tris pH=7.5, 10 mM $MgCl_2$, 150 mM NaCl and 0.1% (v/v) TritonX are performed.

Automated Fluidics Design

Each cycle involves the following steps:
1. Removal of solution in well and delivery of dye-oligonucleotide set
2. Hybridization incubation
3. Removal of dye-oligonucleotide set solution and washing of sample (4×)
4. Sample imaging
5. Removal of solution in well and delivery of formamide solution
6. Formamide solution incubation
7. Removal of solution in well and washing of sample (4×)
8. Removal of solution in well and delivery of formamide solution
9. Formamide solution incubation
10. Removal of solution in well and washing of sample (4×)
11. Removal of solution in well and delivery of formamide solution
12. Formamide solution incubation
13. Removal of solution in well and washing of sample (4×)

This process is fully automated using a pump system controlled by a custom built electronic board/python program in combination with a 96-well plate compatible autosampler.

EXAMPLE 1

Figure 2:
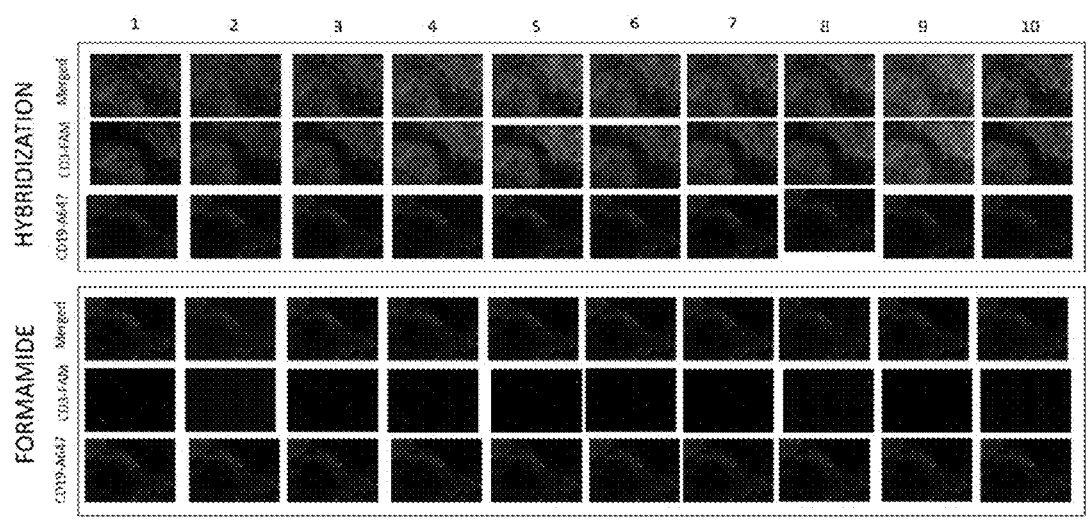
FIG. 2: Dye-oligonucleotide hybridization/removal to DNA-conjugated antibody. A human fresh-frozen lymph node tissue was stained with a DNA-conjugated CD3 antibody and an Alexa647-conjugated CD19 antibody. Both merged and individual FITC/A647 channels are shown for the same region of tissue across ten cycles of hybridization/formamide removal.
Figure 3:
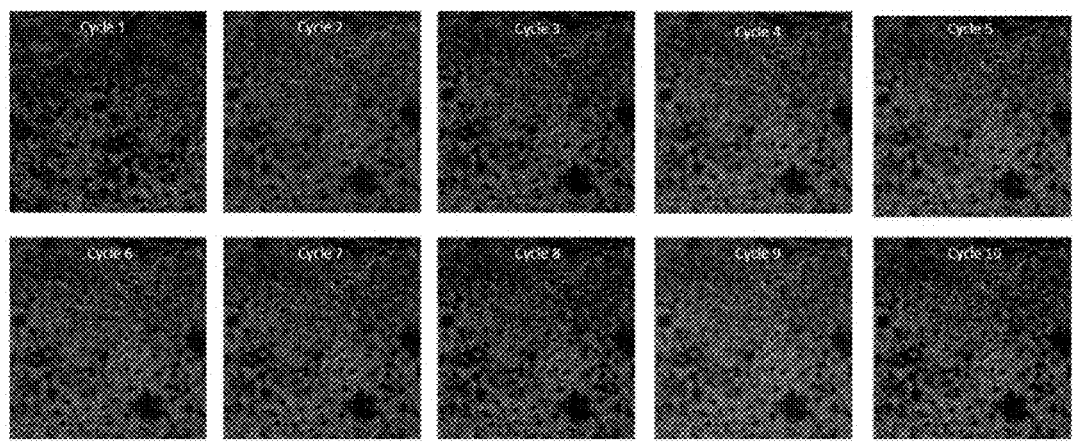
FIG. 3: Iterative cycles of hybridization give consistent staining pattern. A zoomed in region of the merged images from FIG. 2 is shown. The CD3 staining shown by the hybridization of a FITC-oligonucleotide to a DNA-conjugated CD3 antibody is equivalent across ten cycles.

Dye-oligonucleotide can be Hybridized to Antibody-DNA Conjugate and Removed Over Repeated Cycles The basis of this technology is the ability to anneal and remove dye-labeled oligonucleotides to/from a DNA-conjugated antibody. To prove the feasibility of this, a human fresh-frozen lymph node tissue was stained with a DNA-conjugated CD3 antibody (clone UCHT1). A directly dye-labeled (Alexa647) antibody against CD19 was used as a counterstain. Iterative cycles of annealing/de-hybridization were performed. The same region of tissue was visualized on a Keyence microscope after both the hybridization/formamide steps. During each cycle, a complementary FAM-labeled oligonucleotide against the CD3 conjugated sequence (14 nt, Tm=42.4° C.). was allowed to hybridize for five minutes at room temperature (~23° C.). Formamide solution (30%) was added to the tissue and incubated for five minutes to remove the dye-labeled oligonucleotide (FIGS. 2&3).

EXAMPLE 2

DNA-oligonucleotide Hybridization Kinetics

Figure 4:
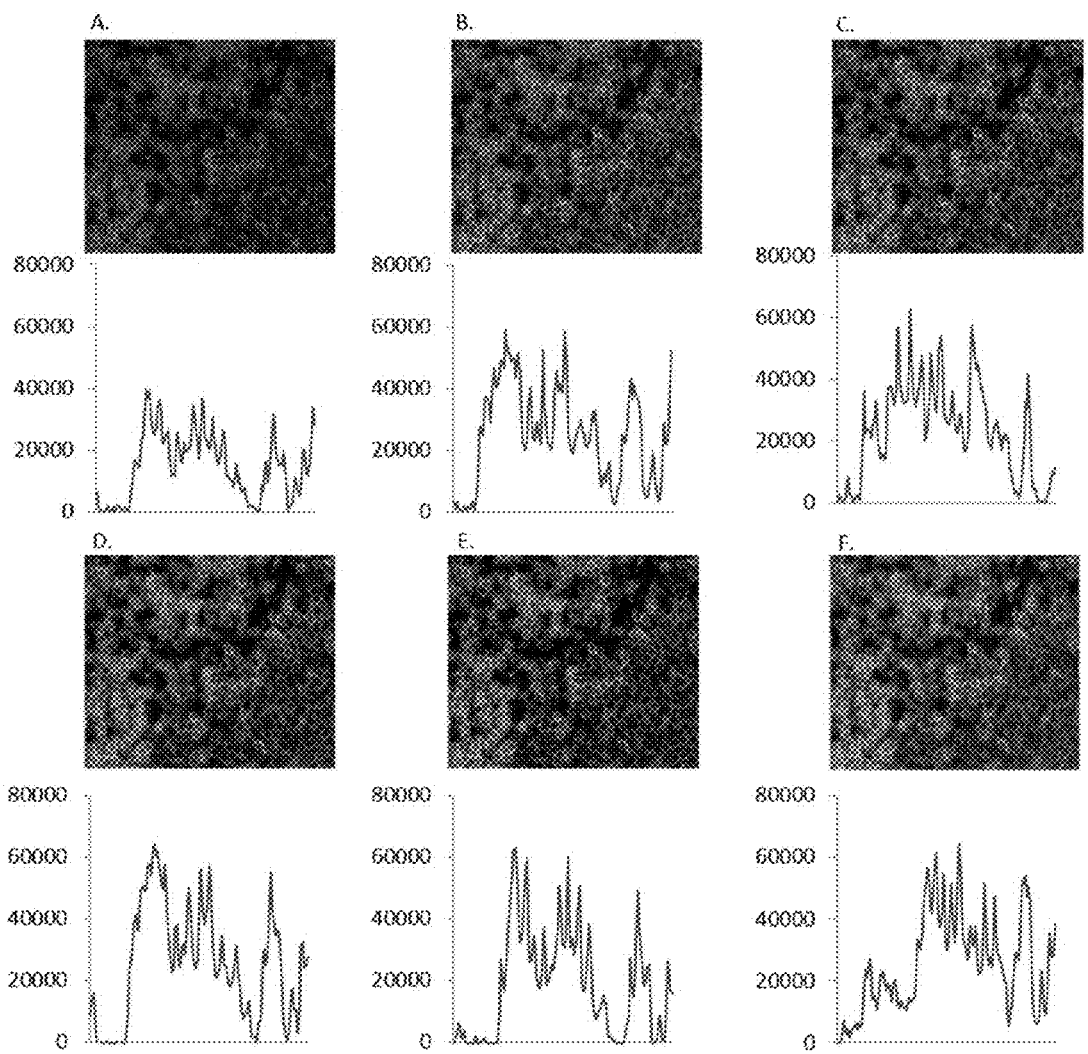
FIG. 4: DNA-oligonucleotide hybridization kinetics. Fluorescence intensity was measured after hybridization of a FITC-labeled oligonucleotide complementing the DNA-conjugated CD3 antibody. Hybridization efficiency was measured across six time points: 30 seconds (A), 1 minute (B), 2 minutes (C), 5 minutes (D), 10 minutes (E) and 20 minutes (F).

The utility in this technology is improved with decreased time per cycle. To determine the minimal hybridization time, a fresh-frozen human lymph node tissue was stained with a DNA-conjugated CD3 antibody and an Alexa647 conjugated CD19 antibody. The complementary FITC-labeled oligonucleotide was added to the tissue (1 µM) for different incubation times and the cell staining intensity was measured. Each hybridization incubation was followed by a formamide incubation (30%) to remove all hybridized oligonucleotide. The same tissue region was imaged for all tested incubation times for direct fluorescence intensity comparison. Within two minutes of hybridization, the fluorescence intensity was maximized (FIG. 4).

EXAMPLE 3

Formamide Removal Kinetics

Figure 5:
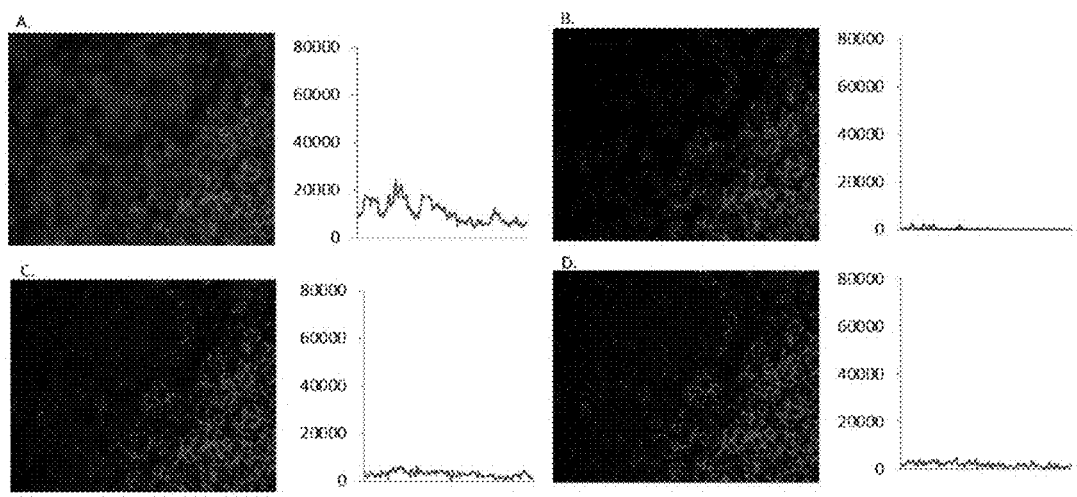
FIG. 5: Dye-labeled oligonucleotide removal by formamide kinetics. The tissue used in FIG. 4 was used to measure the minimum time to remove the dye-oligonucleotide hybridized to the DNA-conjugated CD3 antibody. Four time points were tested: 30 seconds (A), 1 minute1 (B), 2.5 minutes (C) and 55 minutes (D).

Each cycle involves both a hybridization step and removal step using formamide The minimum amount of time to remove all hybridized dye-labeled oligonucleotides was determined. The same tissue that was used to test the hybridization kinetics was used to test the formamide removal kinetics. The complementary dye-labeled oligonucleotide (1 µM) was hybridized for five minutes. Formamide solution (30%) was incubated for different time periods after which the solution was washed away to halt the removal (FIG. 5). Between each time point tested, additional dye-labeled oligonucleotide was added. After one minute, the dye-labeled oligonucleotide was completely removed.

EXAMPLE 4

Dye-oligonucleotide Characteristics: Length, Tm

Figure 6:
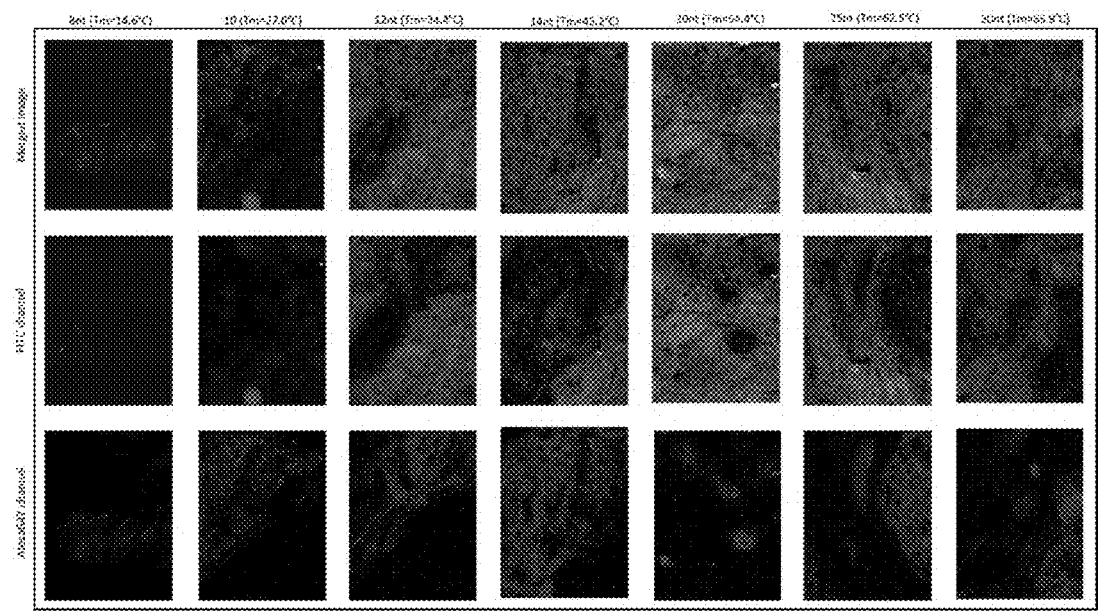
FIG. 6: Dye-labeled oligonucleotide hybridization efficiency as a function of length/Tm. Dye-labeled oligonucleotides complementing the DNA-conjugated CD3 antibody were designed with various lengths (8-30 nt) and corresponding Tms (14.6-65.9° C., respectively). Each probe was hybridized to a different human lymph node tissue section stained with CD19-Alexa647 and DNA-conjugated CD3. The hybridization efficiency was measured by the resultant FITC fluorescence intensity.
Figure 7:
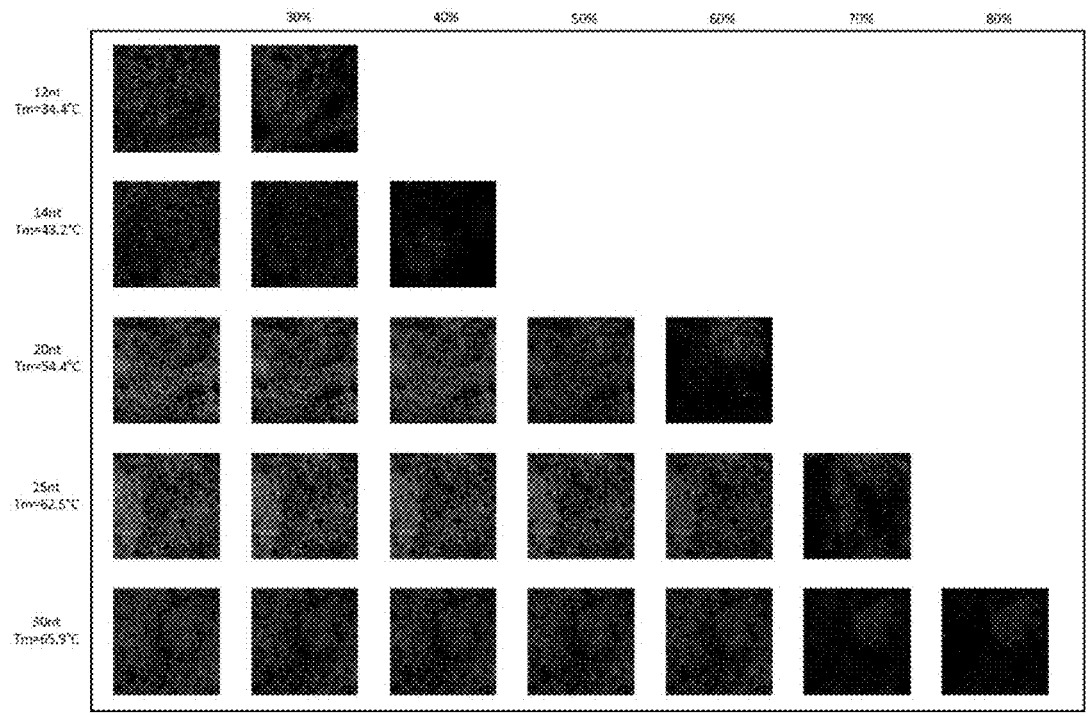
FIG. 7: Dye-labeled oligonucleotide formamide removal efficiency as a function of length/Tm. The minimum formamide solution to remove hybridized dye-labeled oligonucleotides was measured by loss of FITC fluorescence (green).

Preliminary studies measuring the feasibility of repeated cycles of hybridization/removal were performed with a 14 nt complementary dye-labeled oligonucleotide with a Tm=42.4° C. To determine the minimum length/Tm to achieve sufficient antibody staining for the duration of imaging (up to two hours) and the maximum length that can be removed with formamide solution, dye-labeled oligonucleotides of varying lengths were tested for both hybridization propensity/removal (FIGS. 5 and 6). It was found that dye-labeled oligonucleotides with Tms below 28° C. with a length of 10 nt did not hybridize efficiently to the tissue stained with a CD3 DNA-conjugated antibody under the conditions used (FIG. 6). The oligonucleotide with the next closest characteristics, 12 nt in length and a Tm=34.4° C., hybridized as efficiently as all other longer dye-labeled oligonucleotides tested. Each of the hybridized dye-labeled oligonucleotides was incubated with formamide solutions for two minute intervals (FIG. 7). The longest dye-labeled oligonucleotide tested was 30 nt with a Tm=65.9° C. This probe was efficiently removed in an 80% formamide solution. Based on these findings, optimal dye-labeled oligonucleotides for this assay should have a Tm of at least 35° C.

EXAMPLE 5

Figure 9:
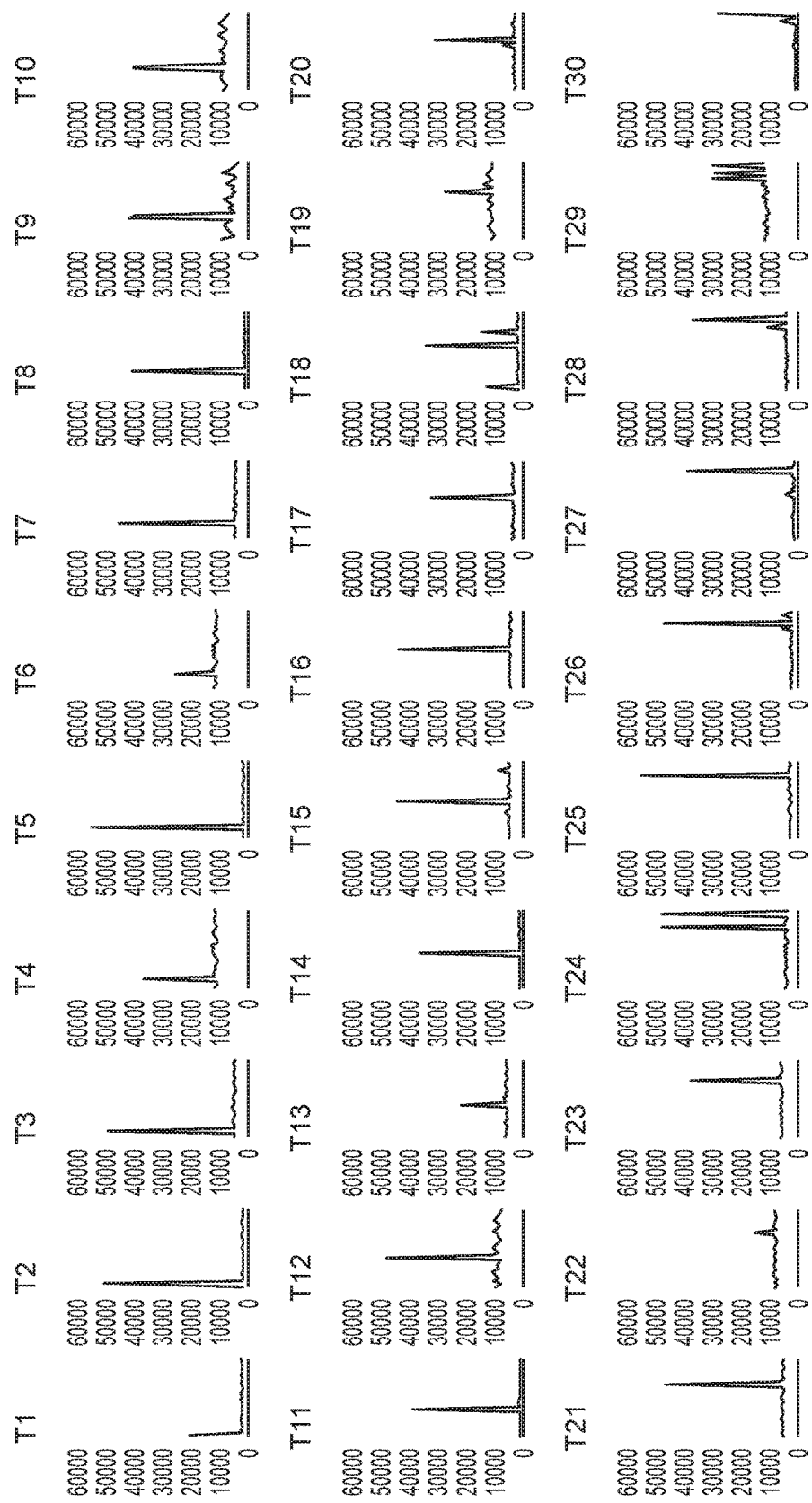
FIG. 9: Representative cell traces for each oligonucleotide pair. Cells with positive fluorescence intensity were screened against all other cycles. The color of each trace corresponds to the dye modification: green=FITC, blue=Cy3, red=Cy5.
Figure 10:
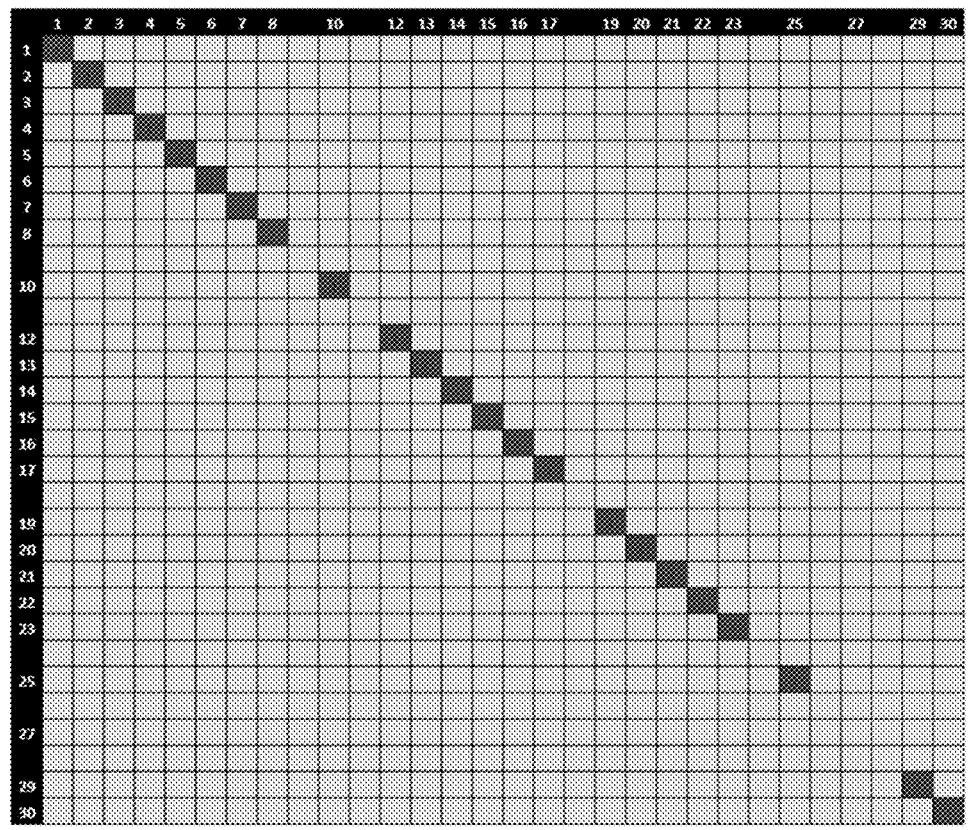
FIG. 10: First-generation of sequence orthogonal oligonucleotide pairs.

Design of Library of Sequence Orthogonal Oligonucleotide Pairs for Antibody Conjugation Each oligonucleotide pair consists of an oligonucleotide conjugated to an antibody and a complementary sequence with a dye modification. The oligonueclodtide bound to antibody is longer in length than the dye-labeled oligonucleotide to allow a tether sequence so that the hybridization does not need to take place right next to the antibody. A library of 30 oligonucleotide pairs was designed and synthesized. To screen for cross-hybridization, each maleimide oligonucleotide was conjugated to a mouse CD45 antibody. Aliquots of mouse spleen cells were stained with a single oligonucleotide labeled CD45 antibody. After sufficient washes, the cells were combined and placed on a coverslip. Iterative cycles of hybridization of sets of three dye-labeled oligonucleotides were performed. Removal of dye-labeled oligonucleotides was performed in between each hybridization using formamide. Fluorescence intensities across cells corresponding to each dye-labeled oligonucleotide was measured and compared with fluorescence intensities corresponding to all other dye-labeled oligonucleotides. The fluorescence intensity values are plotted in FIG. 8. A representative trace of the fluorescence intensity profile for each cell population is given in FIG. 9. Some of the oligonucleotide pairs show cross-hybridization activity (T9 and T10, ee.g.). Based on the fluorescence intensity data given in FIG. 8, a minimum set of oligonucleotide pairs were removed from the library of 30 to create a sequence-orthogonal library set. The resultant library of 24 oligonucleotide pairs is shown in FIG. 10.

Additional oligonucleotide pairs were designed and screened similar to the first set of probes. Currently, there are 45 sequence orthogonal probe sets.

EXAMPLE 6

Automated Fluidics Setup

Figure 11:
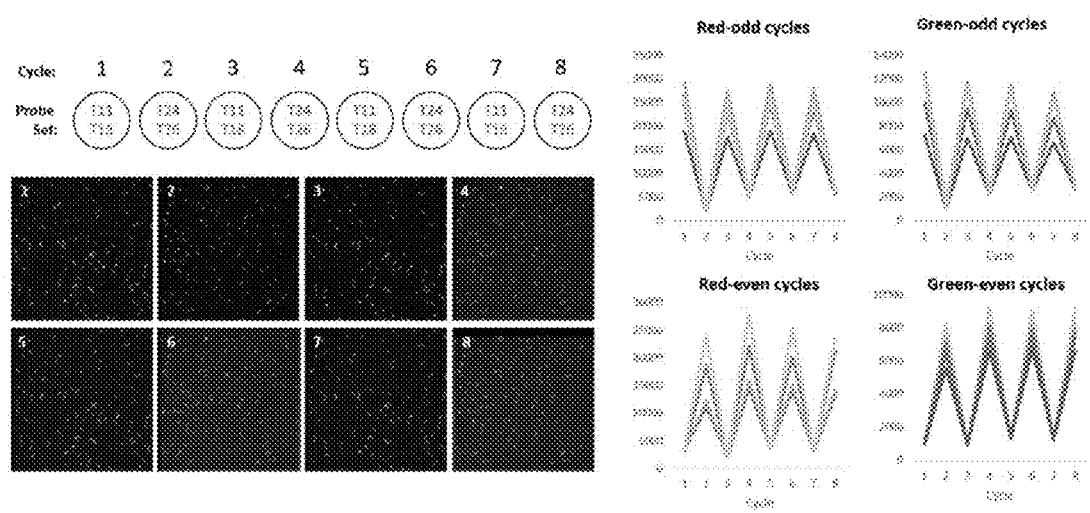
FIG. 11: Automated fluidics setup screening. Pairs of dye-oligonucleotides were placed in odd/even numbered wells on a 96 well plate. Each fluidic cycle delivered either T11-Cy5 and T18-Cy3 or T24-Cy5 and T26-Cy3. Five representative cell traces are plotted.

Each cycle involves delivery of three types of solution to the sample well: 1) oligonucleotide mix, 2) wash solution and 3) formamide solution. For ease of use and reproducibility purposes, the fluidics was fully automated. An autosampler was programmed in line with a series of pumps controlling each solution. At each cycle, the corresponding set of three oligonucleotides is withdrawn from a designated well within a 96-well plate. The solution is pumped to the sample and incubated. The entire set of commands to complete a single cycle is fully automated and controlled by a python program. To demonstrate the use of the autosampler, pairs of dye-labeled oligonucleotides were added to the first eight positions in the 96-well plate. Each odd cycle well contains dye-oligonucleotides T11-cy5 and T18-cy3, while each even cycle contains T24-Cy5 and T26-Cy3. Populations of mouse spleen cells stained with CD45 antibodies conjugated to different oligonucleotides were imaged using this platform. Images of stained cells from each cycle are shown in FIG. 11 as well as representative cell traces across five cells from each population. As shown, the fluorescence intensity is equivalent across all odd and even cycles, indicating the autosampler delivers the dye-labeled oligonucleotide solution to the sample without any carryover.

EXAMPLE 7

Staining Human Tissues Using Antibodies Conjugated to Oligonucleotide Library

Figure 12:
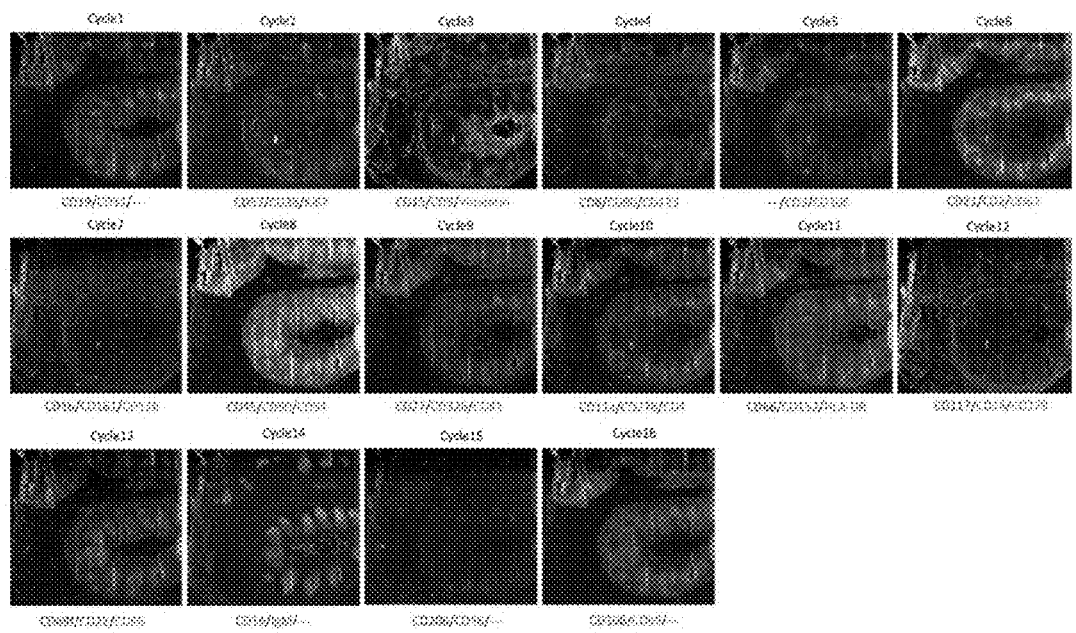
FIG. 12: Multiplexed immune fluorescence staining of human tonsil using cycles of annealing/removal of dye-labeled oligonucleotides.
Figure 13:
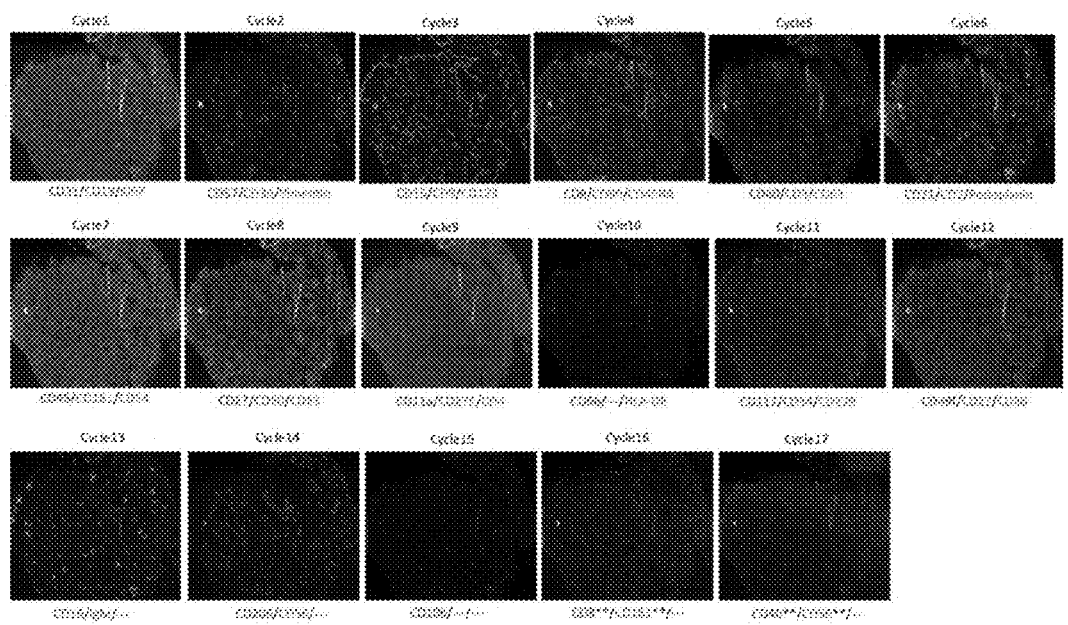
FIG. 13: Multiplexed immune fluorescence staining of human tonsil using cycles of annealing/removal of dye-labeled oligonucleotides.

Human tissues were stained with a cocktail of antibodies conjugated to one of the maleimide oligonucleotides. Iterative cycles of hybridization/removal were performed with imaging occurring after each hybridization step. A human tonsil (FIG. 12) and human lymph node (FIG. 13) were imaged using this platform. Expected staining occurred in nearly every cycle.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for analyzing a sample comprising fixed cells, comprising the following steps, performed in order:
   (a) obtaining:
      i. a plurality of capture agents that are each linked to a different oligonucleotide; and
      ii. a corresponding plurality of labeled nucleic acid probes, wherein each of the labeled nucleic acid probes specifically hybridizes with only one of the oligonucleotides of (a)(i);
   (b) labeling the sample comprising fixed cells with the plurality of capture agents of (a)(i);
   (c) specifically hybridizing a first sub-set of the labeled nucleic acid probes of (a)(ii) with the sample comprising fixed cells, wherein the probes in the first sub-set are distinguishably labeled, to produce labeled probe/oligonucleotide duplexes;
   (d) reading the sample comprising fixed cells to obtain an image showing binding pattern for each of the probes hybridized in step (c);
   (e) completely removing the probes hybridized in step (c) from the sample comprising fixed cells by denaturation by incubating the sample in 70%-90% of a chemical denaturant in the absence of heating, wherein the chemical denaturant is DMSO or formamide and the denaturation is not by displacing the DNA probes using displacement probes, leaving the plurality of capture agents of (b) and their associated oligonucleotides still bound to the sample comprising fixed cells; and
   (f) repeating steps (c) and (d) multiple times with a different sub-set of the labeled nucleic acid probes of (a)(ii), each repeat followed by step (e) except for the final repeat, to produce a plurality of images of the sample comprising fixed cells, each image corresponding to a different sub-set of labeled nucleic acid probes used in (c).

2. The method of claim 1, wherein the sample is a planar cellular sample.

3. The method of claim 1, wherein the oligonucleotides of (a)(i) are at least 5 nucleotides in length.

4. The method of claim 1, wherein the labeled nucleic acid probes of (a)(ii) are at least 5 nucleotides in length.

5. The method of claim 1, wherein sequences of the oligonucleotides to which the capture agents of (a)(i) are linked are: i. longer than sequences of the labeled nucleic acid probes of (a)(ii) and ii. otherwise identical to one other except for a sub-sequence that is complementary to a single labeled nucleic acid probe of (a)(ii).

6. The method of claim 1, wherein the probe/oligonucleotide duplexes of (c) have a $T_m$ of at least 15° C.

7. The method of claim 1, wherein the hybridizing of (c) is for a period of time of about 2 minutes.

8. The method of claim 1, wherein each labeled nucleic acid probe has a sequence selected from SEQ ID NOS: 1-47, or a complement thereof.

9. The method of claim 1, wherein each oligonucleotide linked to a capture agent is selected from SEQ ID NOS: 48-94, or a complement thereof.

10. The method of claim 1, wherein the plurality of capture agents is at least 10 capture agents.

11. The method of claim 1, wherein each different sub-set is independently 2 to 4 labeled nucleic acid probes.

12. The method of claim 1, wherein the probes are removed in step (e) by incubating the sample in 70% to 90% formamide for a period of at least 1 minute, followed by a wash.

13. The method of claim 1, wherein step (f) comprises repeating steps (c) and (d) 2 to 20 times.

14. The method of claim 1, further comprising analyzing at least two of the images.

15. The method of claim 14, wherein the analyzing comprises comparing or overlaying at least two images of the plurality of images.

16. The method of claim 1, further comprising overlaying all of the plurality of images to produce an image showing the pattern of binding of all of the plurality capture agents to the planar sample.

17. The method of claim 1, wherein the labeled nucleic acid probes are fluorescently labeled.

18. The method of claim 1, wherein reading is done by fluorescence microscopy.

19. The method of claim 1, wherein the capture agent is antibody or aptamer.

20. The method of claim 1, wherein the planar sample is a formalin-fixed, paraffin-embedded (FFPE) section.

21. The method of claim 1, wherein (f) comprises repeating steps (c) and (d) at least 5 times with the different sub-set of the labeled nucleic acid probes of (a)(ii).

* * * * *